United States Patent
Thacker et al.

(10) Patent No.: US 11,382,531 B2
(45) Date of Patent: Jul. 12, 2022

(54) SYSTEMS AND METHODS FOR POSITIONING IMPLANTED DEVICES IN A PATIENT

(71) Applicant: Nevro Corp., Redwood City, CA (US)

(72) Inventors: James R. Thacker, Homer, AK (US); Jon Parker, San Jose, CA (US); Yougandh Chitre, Santa Clara, CA (US)

(73) Assignee: Nevro Corp., Redwood City, CA (US)

(*) Notice: Subject to any disclaimer, the term of this patent is extended or adjusted under 35 U.S.C. 154(b) by 514 days.

(21) Appl. No.: 16/287,486

(22) Filed: Feb. 27, 2019

(65) Prior Publication Data
US 2019/0320936 A1    Oct. 24, 2019

Related U.S. Application Data

(63) Continuation of application No. 15/148,987, filed on May 6, 2016, now abandoned, which is a continuation
(Continued)

(51) Int. Cl.
*A61B 5/06* (2006.01)
*A61N 1/36* (2006.01)
(Continued)

(52) U.S. Cl.
CPC ............... *A61B 5/065* (2013.01); *A61B 5/063* (2013.01); *A61B 5/066* (2013.01); *A61B 5/407* (2013.01);
(Continued)

(58) Field of Classification Search
CPC ..... A61M 2025/0166; A61B 2019/462; A61B 2019/5246; A61B 2019/5251;
(Continued)

(56) References Cited

U.S. PATENT DOCUMENTS

| 3,195,540 A | 7/1965 | Waller et al. |
| 3,724,467 A | 4/1973 | Avery et al. |

(Continued)

FOREIGN PATENT DOCUMENTS

| CN | 101920065 A | 12/2010 |
| EP | 0158316 A2 | 10/1985 |

(Continued)

OTHER PUBLICATIONS

International Search Report and Written Opinion for International Patent Application No. PCT/US11/53714, Applicant: Nevro Corporation, dated Aug. 10, 2012, 14 pages.
(Continued)

*Primary Examiner* — Eugene T Wu
(74) *Attorney, Agent, or Firm* — Perkins Coie LLP

(57) ABSTRACT

Systems and methods for positioning implanted devices in a patient are disclosed. A method in accordance with a particular embodiment includes, for each of a plurality of patients, receiving a target location from which to deliver a modulation signal to the patient's spinal cord. The method further includes implanting a signal delivery device within a vertebral foramen of each patient, and positioning an electrical contact carried by the signal delivery device to be within ±5 mm. of the target location, without the use of fluoroscopy. The method can still further include, for each of the plurality of patients, activating the electrical contact to modulate neural activity at the spinal cord. In further particular embodiments, RF signals, ultrasound, magnetic fields, and/or other techniques are used to locate the signal delivery device.

27 Claims, 9 Drawing Sheets

Related U.S. Application Data of application No. 14/598,114, filed on Jan. 15, 2015, now Pat. No. 9,345,891, which is a continuation of application No. 12/895,403, filed on Sep. 30, 2010, now Pat. No. 8,965,482.

(51) Int. Cl.
  *A61N 1/372* (2006.01)
  *A61B 34/20* (2016.01)
  *A61B 5/00* (2006.01)
  *A61B 90/00* (2016.01)

(52) U.S. Cl.
  CPC .............. *A61B 34/20* (2016.02); *A61B 90/06* (2016.02); *A61N 1/36071* (2013.01); *A61N 1/36128* (2013.01); *A61N 1/36185* (2013.01); *A61N 1/37217* (2013.01); *A61N 1/37241* (2013.01); *A61B 2034/2051* (2016.02); *A61B 2034/2072* (2016.02); *A61B 2090/062* (2016.02); *A61B 2560/045* (2013.01)

(58) Field of Classification Search
  CPC .... A61B 2019/5253; A61B 2019/5259; A61B 2019/5272; A61B 2019/5289; A61B 2019/5219; A61B 2019/5293; A61B 2019/4894; A61B 19/5244; A61B 19/5225; A61B 5/061; A61B 5/062; A61B 5/063; A61B 5/065; A61B 5/066; A61B 5/068; A61B 5/742–745; A61B 5/6801–6844
  See application file for complete search history.

(56) References Cited

U.S. PATENT DOCUMENTS

| | | | |
|---|---|---|---|
| 3,774,618 A | 11/1973 | Avery | |
| 3,796,221 A | 3/1974 | Hagfors | |
| 4,096,866 A | 6/1978 | Fischell | |
| 4,136,703 A | 1/1979 | Wittkampf | |
| 4,141,365 A | 2/1979 | Fischell et al. | |
| 4,282,886 A | 8/1981 | King | |
| 4,328,813 A | 5/1982 | Ray | |
| 4,355,224 A | 10/1982 | Mesick et al. | |
| 4,422,917 A | 12/1983 | Hayfield | |
| 4,432,377 A | 2/1984 | Dickhudt | |
| 4,462,401 A | 7/1984 | Burgio | |
| 4,462,402 A | 7/1984 | Burgio et al. | |
| 4,465,079 A | 8/1984 | Dickhudt | |
| 4,498,482 A | 2/1985 | Williams | |
| 4,515,168 A | 5/1985 | Chester et al. | |
| 4,538,624 A | 9/1985 | Tarjan | |
| 4,573,448 A | 3/1986 | Kambin | |
| 4,573,481 A | 3/1986 | Bullara | |
| 4,579,120 A | 4/1986 | MacGregor | |
| 4,603,696 A | 8/1986 | Cross, Jr. et al. | |
| 4,658,835 A | 4/1987 | Pohndorf | |
| 4,683,895 A | 8/1987 | Pohndorf | |
| 4,721,551 A | 1/1988 | Byers et al. | |
| 4,744,370 A | 5/1988 | Harris | |
| 4,744,371 A | 5/1988 | Harris | |
| 4,764,132 A | 8/1988 | Stutz, Jr. | |
| 4,796,642 A | 1/1989 | Harris | |
| 4,830,776 A | 5/1989 | Thompson | |
| 4,919,653 A | 4/1990 | Martinez et al. | |
| 4,920,979 A | 5/1990 | Bullara | |
| 4,926,878 A | 5/1990 | Snedeker | |
| 4,934,383 A | 6/1990 | Glumac | |
| 4,940,065 A | 7/1990 | Tanagho et al. | |
| 4,961,434 A | 10/1990 | Stypulkowski | |
| 4,979,511 A | 12/1990 | Terry, Jr. | |
| 5,000,194 A | 3/1991 | Van den Honert et al. | |
| 5,007,902 A | 4/1991 | Witt | |
| 5,036,862 A | 8/1991 | Pohndorf | |
| 5,042,486 A | 8/1991 | Pfeiler et al. | |
| 5,046,511 A | 9/1991 | Maurer et al. | |
| 5,072,458 A * | 12/1991 | Suzuki | A61B 5/02755 2/102 |
| 5,078,140 A | 1/1992 | Kwoh | |
| 5,159,926 A | 11/1992 | Ljungstroem | |
| 5,205,297 A | 4/1993 | Montecalvo et al. | |
| 5,211,165 A | 5/1993 | Dumoulin et al. | |
| 5,257,636 A | 11/1993 | White | |
| 5,265,608 A | 11/1993 | Lee et al. | |
| 5,273,053 A | 12/1993 | Pohndorf | |
| 5,306,236 A | 4/1994 | Blumenfeld et al. | |
| 5,314,458 A | 5/1994 | Najafi et al. | |
| 5,325,873 A | 7/1994 | Hirschi et al. | |
| 5,351,394 A | 10/1994 | Weinberg | |
| 5,351,687 A | 10/1994 | Kroll et al. | |
| 5,351,697 A | 10/1994 | Cheney et al. | |
| 5,360,441 A | 11/1994 | Otten | |
| 5,366,489 A | 11/1994 | Burgio et al. | |
| 5,375,596 A | 12/1994 | Twiss et al. | |
| 5,425,367 A | 6/1995 | Shapiro et al. | |
| 5,458,629 A | 10/1995 | Baudino et al. | |
| 5,458,631 A | 10/1995 | Xavier | |
| 5,464,446 A | 11/1995 | Dreessen et al. | |
| 5,496,363 A | 3/1996 | Burgio et al. | |
| 5,527,338 A | 6/1996 | Purdy | |
| 5,527,358 A | 6/1996 | Mehmanesh et al. | |
| 5,531,778 A | 7/1996 | Maschino et al. | |
| 5,562,722 A | 10/1996 | Racz et al. | |
| 5,578,074 A | 11/1996 | Mirigian | |
| 5,643,330 A | 7/1997 | Holsheimer et al. | |
| 5,669,882 A | 9/1997 | Pyles | |
| 5,727,553 A | 3/1998 | Saad | |
| 5,728,148 A | 3/1998 | Bostrom et al. | |
| 5,730,628 A | 3/1998 | Hawkins | |
| 5,755,750 A | 5/1998 | Petruska et al. | |
| 5,759,471 A | 6/1998 | Malewicz | |
| 5,760,341 A | 6/1998 | Laske et al. | |
| 5,769,877 A | 6/1998 | Barreras, Sr. | |
| 5,843,148 A | 12/1998 | Gijsbers | |
| 5,846,226 A | 12/1998 | Urmey | |
| 5,848,126 A | 12/1998 | Fujita et al. | |
| 5,865,843 A | 2/1999 | Baudino | |
| 5,871,487 A | 2/1999 | Warner et al. | |
| 5,902,236 A | 5/1999 | Iversen | |
| 5,927,277 A | 7/1999 | Baudino et al. | |
| 5,935,159 A | 8/1999 | Cross, Jr. et al. | |
| 5,957,965 A | 9/1999 | Moumane et al. | |
| 5,957,968 A | 9/1999 | Belden et al. | |
| 5,983,126 A | 11/1999 | Wittkampf | |
| 6,052,623 A | 4/2000 | Fenner et al. | |
| 6,055,456 A | 4/2000 | Gerber | |
| 6,066,165 A | 5/2000 | Racz | |
| 6,078,839 A | 6/2000 | Carson | |
| 6,104,960 A | 8/2000 | Duysens | |
| 6,106,460 A | 8/2000 | Panescu et al. | |
| 6,125,291 A | 9/2000 | Miesel et al. | |
| 6,129,742 A | 10/2000 | Wu et al. | |
| 6,134,459 A | 10/2000 | Roberts et al. | |
| 6,134,477 A | 10/2000 | Knuteson | |
| 6,144,866 A | 11/2000 | Miesel et al. | |
| 6,154,678 A | 11/2000 | Lauro | |
| 6,163,727 A | 12/2000 | Errico | |
| 6,178,357 B1 | 1/2001 | Gliner et al. | |
| 6,185,463 B1 | 2/2001 | Baudino | |
| 6,192,279 B1 | 2/2001 | Barreras, Sr. et al. | |
| 6,198,952 B1 | 3/2001 | Miesel | |
| 6,198,963 B1 | 3/2001 | Haim et al. | |
| 6,205,356 B1 | 3/2001 | Holcomb | |
| 6,210,417 B1 | 4/2001 | Baudino et al. | |
| 6,214,016 B1 | 4/2001 | Williams et al. | |
| 6,216,045 B1 | 4/2001 | Black et al. | |
| 6,249,965 B1 | 6/2001 | Bullara et al. | |
| 6,253,109 B1 | 6/2001 | Gielen | |
| 6,263,230 B1 | 7/2001 | Haynor et al. | |
| 6,292,702 B1 | 9/2001 | King et al. | |
| 6,298,265 B1 | 10/2001 | Burgio | |
| 6,304,785 B1 | 10/2001 | McCreery et al. | |
| 6,308,103 B1 | 10/2001 | Gielen | |

(56) References Cited

U.S. PATENT DOCUMENTS

| | | |
|---|---|---|
| 6,309,401 B1 | 10/2001 | Redko et al. |
| 6,321,104 B1 | 11/2001 | Gielen et al. |
| 6,321,123 B1 | 11/2001 | Morris et al. |
| 6,366,815 B1 | 4/2002 | Haugland et al. |
| 6,393,327 B1 | 5/2002 | Scribner |
| 6,397,108 B1 | 5/2002 | Camps et al. |
| 6,442,435 B2 | 8/2002 | King et al. |
| 6,445,955 B1 | 9/2002 | Michelson et al. |
| 6,456,866 B1 | 9/2002 | Tyler et al. |
| 6,464,682 B1 | 10/2002 | Snoke |
| 6,473,653 B1 | 10/2002 | Schallhorn et al. |
| 6,474,341 B1 | 11/2002 | Hunter et al. |
| 6,477,427 B1 | 11/2002 | Stolz et al. |
| 6,493,590 B1 | 12/2002 | Wessman et al. |
| 6,493,592 B1 | 12/2002 | Leonard et al. |
| 6,516,226 B1 | 2/2003 | Bishay et al. |
| 6,516,227 B1 | 2/2003 | Meadows et al. |
| 6,516,807 B1 | 2/2003 | Panescu et al. |
| 6,522,927 B1 | 2/2003 | Bishay et al. |
| 6,522,932 B1 | 2/2003 | Kuzma et al. |
| 6,529,774 B1 | 3/2003 | Greene |
| 6,546,293 B2 | 4/2003 | Errico et al. |
| 6,549,797 B1 | 4/2003 | Leonard et al. |
| 6,549,810 B1 | 4/2003 | Leonard et al. |
| 6,549,812 B1 | 4/2003 | Smits |
| 6,556,869 B1 | 4/2003 | Leonard et al. |
| 6,556,873 B1 | 4/2003 | Smits |
| 6,560,491 B1 | 5/2003 | Leonard et al. |
| 6,587,733 B1 | 7/2003 | Cross, Jr. et al. |
| 6,600,956 B2 | 7/2003 | Maschino et al. |
| 6,609,029 B1 | 8/2003 | Mann et al. |
| 6,622,051 B1 | 9/2003 | Bishay et al. |
| 6,714,822 B2 | 3/2004 | King et al. |
| 6,718,211 B2 | 4/2004 | Smits |
| 6,721,604 B1 | 4/2004 | Robinson et al. |
| 6,733,500 B2 | 5/2004 | Kelley et al. |
| 6,741,892 B1 | 5/2004 | Meadows et al. |
| 6,741,893 B2 | 5/2004 | Smits |
| 6,754,539 B1 | 6/2004 | Erickson et al. |
| 6,785,571 B2 | 8/2004 | Glossop et al. |
| 6,847,845 B2 | 1/2005 | Belden |
| 6,875,571 B2 | 4/2005 | Crabtree et al. |
| 6,895,276 B2 | 5/2005 | Kast et al. |
| 6,895,283 B2 | 5/2005 | Erickson et al. |
| 6,907,299 B2 | 6/2005 | Han |
| 6,909,918 B2 | 6/2005 | Stypulkowski |
| 6,934,589 B2 | 8/2005 | Sundquist et al. |
| 6,970,747 B2 | 11/2005 | Kokones et al. |
| 6,980,863 B2 | 12/2005 | Van Venrooij et al. |
| 6,981,314 B2 | 1/2006 | Black et al. |
| 6,993,384 B2 | 1/2006 | Bradley et al. |
| 6,999,820 B2 | 2/2006 | Jordan |
| 7,010,856 B2 | 3/2006 | Suda et al. |
| 7,035,690 B2 | 4/2006 | Goetz |
| 7,047,082 B1 | 5/2006 | Schrom et al. |
| 7,051,419 B2 | 5/2006 | Schrom et al. |
| 7,072,719 B2 | 7/2006 | Vinup et al. |
| 7,107,104 B2 | 9/2006 | Keravel et al. |
| 7,110,827 B2 | 9/2006 | Sage et al. |
| 7,130,696 B2 | 10/2006 | Carter et al. |
| 7,133,722 B2 | 11/2006 | Hansen et al. |
| 7,142,919 B2 | 11/2006 | Hine et al. |
| 7,142,925 B1 | 11/2006 | Bhadra et al. |
| 7,146,222 B2 | 12/2006 | Boling |
| 7,146,224 B2 | 12/2006 | King |
| 7,149,585 B2 | 12/2006 | Wessman et al. |
| 7,164,951 B2 | 1/2007 | Ries et al. |
| 7,174,219 B2 | 2/2007 | Wahlstrand et al. |
| 7,184,838 B2 | 2/2007 | Cross, Jr. |
| 7,184,840 B2 | 2/2007 | Stolz et al. |
| 7,187,981 B2 | 3/2007 | Tanaka |
| 7,206,642 B2 | 4/2007 | Pardo et al. |
| 7,211,103 B2 | 5/2007 | Greenberg et al. |
| 7,212,867 B2 | 5/2007 | Van Venrooij et al. |
| 7,236,834 B2 | 6/2007 | Christopherson et al. |
| 7,244,150 B1 | 7/2007 | Brase et al. |
| 7,282,033 B2 | 10/2007 | Urmey |
| 7,299,095 B1 | 11/2007 | Barlow et al. |
| 7,363,076 B2 | 4/2008 | Yun et al. |
| 7,363,089 B2 | 4/2008 | Vinup et al. |
| 7,379,776 B1 | 5/2008 | Chitre et al. |
| 7,381,441 B2 | 6/2008 | Leung et al. |
| 7,383,090 B2 | 6/2008 | O'Brien et al. |
| 7,386,350 B2 | 6/2008 | Vilims |
| 7,421,297 B2 | 9/2008 | Giftakis et al. |
| 7,425,142 B1 | 9/2008 | Putz |
| 7,455,666 B2 | 11/2008 | Purdy |
| 7,463,917 B2 | 12/2008 | Martinez |
| 7,493,159 B2 | 2/2009 | Hrdlicka et al. |
| 7,499,755 B2 | 3/2009 | Cross, Jr. |
| 7,502,652 B2 | 3/2009 | Gaunt et al. |
| 7,584,004 B2 | 9/2009 | Caparso et al. |
| 7,590,454 B2 | 9/2009 | Garabedian et al. |
| 7,613,524 B2 | 11/2009 | Jordan |
| 7,617,003 B2 | 11/2009 | Caparso et al. |
| 7,623,919 B2 | 11/2009 | Goetz et al. |
| 7,676,273 B2 | 3/2010 | Goetz et al. |
| 7,689,284 B2 | 3/2010 | Imran et al. |
| 7,702,379 B2 | 4/2010 | Avinash et al. |
| 7,769,472 B2 | 8/2010 | Gerber |
| 7,781,806 B2 | 8/2010 | VanBuskirk et al. |
| 7,810,233 B2 | 10/2010 | Krulevitch et al. |
| 7,810,996 B1 | 10/2010 | Giphart et al. |
| 7,831,307 B1 | 11/2010 | Moffitt |
| 7,844,343 B2 | 11/2010 | Wahlstrand et al. |
| 7,853,330 B2 | 12/2010 | Bradley et al. |
| 7,860,568 B2 | 12/2010 | Deininger et al. |
| 7,881,806 B2 | 2/2011 | Horrigan et al. |
| 7,957,808 B2 | 6/2011 | Dawant et al. |
| 7,996,055 B2 | 8/2011 | Hauck et al. |
| 8,010,207 B2 | 8/2011 | Smits et al. |
| 8,019,439 B2 | 9/2011 | Kuzma et al. |
| 8,036,756 B2 | 10/2011 | Swoyer et al. |
| 8,060,207 B2 | 11/2011 | Wallace et al. |
| 8,078,280 B2 | 12/2011 | Sage |
| 8,131,357 B2 | 3/2012 | Bradley et al. |
| 8,197,494 B2 | 6/2012 | Jaggi et al. |
| 8,224,459 B1 | 7/2012 | Pianca et al. |
| 8,255,057 B2 | 8/2012 | Fang et al. |
| 8,303,502 B2 | 11/2012 | Washburn et al. |
| 8,355,791 B2 | 1/2013 | Moffitt |
| 8,355,797 B2 | 1/2013 | Caparso et al. |
| 8,494,652 B2 | 7/2013 | Cantlon et al. |
| 8,548,601 B2 | 10/2013 | Chinn et al. |
| 8,634,934 B2 | 1/2014 | Kokones et al. |
| 8,676,331 B2 | 3/2014 | Parker |
| 8,682,447 B2 | 3/2014 | Bradley |
| 8,731,671 B2 | 5/2014 | Rodby et al. |
| 8,913,804 B2 | 12/2014 | Blum et al. |
| 8,965,482 B2 | 2/2015 | Thacker et al. |
| 9,002,460 B2 | 4/2015 | Parker |
| 9,345,891 B2 | 5/2016 | Thacker et al. |
| 9,358,390 B2 | 6/2016 | Polefko et al. |
| 9,403,020 B2 | 8/2016 | Wingeier |
| 9,433,795 B2 | 9/2016 | Lui et al. |
| 9,604,059 B2 | 3/2017 | Parker |
| 10,076,665 B2 | 9/2018 | Parker et al. |
| 2001/0023368 A1 | 9/2001 | Black et al. |
| 2001/0025192 A1 | 9/2001 | Gerber et al. |
| 2001/0027336 A1 | 10/2001 | Gielen et al. |
| 2001/0053885 A1 | 12/2001 | Gielen et al. |
| 2002/0022872 A1 | 2/2002 | Gielen et al. |
| 2002/0052640 A1 | 5/2002 | Bigus et al. |
| 2002/0111661 A1 | 8/2002 | Cross et al. |
| 2002/0173718 A1* | 11/2002 | Frisch .............. A61B 5/073 |
| | | 600/424 |
| 2002/0177887 A1 | 11/2002 | Krebs |
| 2003/0032997 A1 | 2/2003 | Pianca et al. |
| 2003/0055476 A1 | 3/2003 | Vinup et al. |
| 2003/0083697 A1 | 5/2003 | Baudino et al. |
| 2003/0083724 A1 | 5/2003 | Jog et al. |
| 2003/0097165 A1 | 5/2003 | Krulevitch et al. |
| 2003/0097166 A1 | 5/2003 | Krulevitch et al. |
| 2003/0114752 A1 | 6/2003 | Henderson et al. |

(56) References Cited

U.S. PATENT DOCUMENTS

| | | |
|---|---|---|
| 2003/0120150 A1 | 6/2003 | Govari |
| 2003/0136418 A1 | 7/2003 | Behm |
| 2003/0199949 A1 | 10/2003 | Pardo |
| 2003/0199951 A1 | 10/2003 | Pardo et al. |
| 2003/0199952 A1 | 10/2003 | Stolz et al. |
| 2003/0199953 A1 | 10/2003 | Stolz et al. |
| 2003/0199962 A1 | 10/2003 | Struble et al. |
| 2003/0208247 A1 | 11/2003 | Spinelli et al. |
| 2003/0229387 A1 | 12/2003 | Cross et al. |
| 2003/0233134 A1 | 12/2003 | Greenberg et al. |
| 2004/0015205 A1 | 1/2004 | Whitehurst et al. |
| 2004/0015206 A1 | 1/2004 | Bishay et al. |
| 2004/0024439 A1 | 2/2004 | Riso |
| 2004/0024440 A1 | 2/2004 | Cole |
| 2004/0087877 A1 | 5/2004 | Besz et al. |
| 2004/0088033 A1 | 5/2004 | Smits et al. |
| 2004/0088034 A1 | 5/2004 | Smits et al. |
| 2004/0093053 A1 | 5/2004 | Gerber et al. |
| 2004/0097803 A1 | 5/2004 | Panescu |
| 2004/0111139 A1 | 6/2004 | McCreery |
| 2004/0127942 A1 | 7/2004 | Yomtov et al. |
| 2004/0162601 A1 | 8/2004 | Smits |
| 2004/0176683 A1 | 9/2004 | Whitin et al. |
| 2004/0186528 A1 | 9/2004 | Ries et al. |
| 2004/0186543 A1 | 9/2004 | King et al. |
| 2004/0186544 A1 | 9/2004 | King |
| 2004/0215288 A1 | 10/2004 | Lee et al. |
| 2004/0215301 A1 | 10/2004 | Lokhoff et al. |
| 2004/0215305 A1 | 10/2004 | Sage |
| 2004/0215307 A1 | 10/2004 | Michels et al. |
| 2004/0243206 A1 | 12/2004 | Tadlock |
| 2005/0004638 A1 | 1/2005 | Cross |
| 2005/0004639 A1 | 1/2005 | Erickson |
| 2005/0015128 A1 | 1/2005 | Rezai et al. |
| 2005/0021119 A1 | 1/2005 | Sage et al. |
| 2005/0027325 A1 | 2/2005 | Lahti et al. |
| 2005/0027338 A1 | 2/2005 | Hill |
| 2005/0027339 A1 | 2/2005 | Schrom et al. |
| 2005/0027340 A1 | 2/2005 | Schrom et al. |
| 2005/0027341 A1 | 2/2005 | Schrom et al. |
| 2005/0033371 A1 | 2/2005 | Sommer et al. |
| 2005/0049486 A1 | 3/2005 | Urquhart et al. |
| 2005/0049663 A1 | 3/2005 | Harris et al. |
| 2005/0049664 A1 | 3/2005 | Harris et al. |
| 2005/0065588 A1 | 3/2005 | Zhao et al. |
| 2005/0070982 A1 | 3/2005 | Heruth et al. |
| 2005/0070987 A1 | 3/2005 | Erickson |
| 2005/0075684 A1 | 4/2005 | Phillips et al. |
| 2005/0075707 A1 | 4/2005 | Meadows et al. |
| 2005/0085870 A1 | 4/2005 | Goroszeniuk |
| 2005/0107859 A1 | 5/2005 | Daglow et al. |
| 2005/0107861 A1 | 5/2005 | Harris et al. |
| 2005/0113882 A1 | 5/2005 | Cameron et al. |
| 2005/0119713 A1 | 6/2005 | Whitehurst et al. |
| 2005/0131506 A1 | 6/2005 | Rezai et al. |
| 2005/0137667 A1 | 6/2005 | Omar-Pasha et al. |
| 2005/0137668 A1 | 6/2005 | Khan |
| 2005/0138791 A1 | 6/2005 | Black et al. |
| 2005/0138792 A1 | 6/2005 | Black et al. |
| 2005/0165465 A1 | 7/2005 | Pianca et al. |
| 2005/0171587 A1 | 8/2005 | Daglow et al. |
| 2005/0192655 A1 | 9/2005 | Black et al. |
| 2005/0203599 A1 | 9/2005 | Garabedian et al. |
| 2005/0209667 A1 | 9/2005 | Erickson et al. |
| 2005/0222642 A1 | 10/2005 | Przybyszewski et al. |
| 2005/0222657 A1 | 10/2005 | Wahlstrand et al. |
| 2005/0222658 A1 | 10/2005 | Hoegh et al. |
| 2005/0222659 A1 | 10/2005 | Olsen et al. |
| 2005/0228221 A1* | 10/2005 | Hirakawa ............ A61B 1/00009 600/101 |
| 2005/0246003 A1 | 11/2005 | Black et al. |
| 2005/0246004 A1 | 11/2005 | Cameron et al. |
| 2006/0004429 A1 | 1/2006 | Mrva et al. |
| 2006/0052765 A1 | 3/2006 | Pyles et al. |
| 2006/0074456 A1 | 4/2006 | Pyles et al. |
| 2006/0089692 A1 | 4/2006 | Cross et al. |
| 2006/0089695 A1 | 4/2006 | Bolea et al. |
| 2006/0089696 A1 | 4/2006 | Olsen et al. |
| 2006/0089697 A1 | 4/2006 | Cross et al. |
| 2006/0111768 A1 | 5/2006 | Wessman et al. |
| 2006/0127158 A1 | 6/2006 | Olson et al. |
| 2006/0168805 A1 | 8/2006 | Hegland et al. |
| 2006/0173262 A1 | 8/2006 | Hegland et al. |
| 2006/0200218 A1 | 9/2006 | Wahlstrand |
| 2006/0247747 A1 | 11/2006 | Olsen et al. |
| 2006/0247748 A1 | 11/2006 | Wahlstrand et al. |
| 2006/0247749 A1 | 11/2006 | Colvin |
| 2006/0253182 A1 | 11/2006 | King |
| 2006/0264122 A1 | 11/2006 | Aman et al. |
| 2006/0265024 A1 | 11/2006 | Goetz et al. |
| 2006/0265025 A1 | 11/2006 | Goetz et al. |
| 2006/0265037 A1 | 11/2006 | Kuzma |
| 2006/0271137 A1 | 11/2006 | Stanton-Hicks |
| 2007/0038052 A1 | 2/2007 | Swoyer et al. |
| 2007/0050004 A1 | 3/2007 | Swoyer et al. |
| 2007/0050005 A1 | 3/2007 | Lauro |
| 2007/0055332 A1 | 3/2007 | Swoyer |
| 2007/0100386 A1 | 5/2007 | Tronnes et al. |
| 2007/0100408 A1 | 5/2007 | Gerber |
| 2007/0106144 A1 | 5/2007 | Squeri |
| 2007/0106289 A1 | 5/2007 | O'Sullivan |
| 2007/0112398 A1 | 5/2007 | Stevenson et al. |
| 2007/0112404 A1 | 5/2007 | Mann et al. |
| 2007/0118198 A1 | 5/2007 | Prager |
| 2007/0149048 A1 | 6/2007 | O'Brien et al. |
| 2007/0150036 A1 | 6/2007 | Anderson |
| 2007/0191903 A1 | 8/2007 | Bruinstroop |
| 2007/0191904 A1 | 8/2007 | Libbus et al. |
| 2007/0203540 A1 | 8/2007 | Goetz et al. |
| 2007/0208394 A1 | 9/2007 | King et al. |
| 2007/0249901 A1 | 10/2007 | Ohline et al. |
| 2007/0260290 A1 | 11/2007 | Hara et al. |
| 2008/0039738 A1 | 2/2008 | Dinsmoor et al. |
| 2008/0058875 A1 | 3/2008 | Greenberg et al. |
| 2008/0097475 A1 | 4/2008 | Jaggi et al. |
| 2008/0125833 A1 | 5/2008 | Bradley et al. |
| 2008/0140087 A1 | 6/2008 | Barbagli |
| 2008/0140152 A1 | 6/2008 | Imran et al. |
| 2008/0183221 A1 | 7/2008 | Burdulis |
| 2008/0215118 A1 | 9/2008 | Goetz et al. |
| 2008/0234791 A1 | 9/2008 | Arle et al. |
| 2008/0262430 A1 | 10/2008 | Anderson et al. |
| 2008/0275467 A1 | 11/2008 | Liao et al. |
| 2008/0300651 A1 | 12/2008 | Gerber et al. |
| 2008/0319311 A1 | 12/2008 | Hamadeh |
| 2009/0024187 A1 | 1/2009 | Erickson et al. |
| 2009/0048638 A1 | 2/2009 | Rey et al. |
| 2009/0125060 A1 | 5/2009 | Rivard et al. |
| 2009/0198306 A1 | 8/2009 | Goetz et al. |
| 2009/0204173 A1* | 8/2009 | Fang ................ A61N 1/36071 607/46 |
| 2009/0204192 A1 | 8/2009 | Carlton et al. |
| 2009/0210029 A1 | 8/2009 | Tsui |
| 2009/0248118 A1 | 10/2009 | Bradley et al. |
| 2009/0270940 A1 | 10/2009 | Deininger et al. |
| 2010/0069736 A1 | 3/2010 | Finneran et al. |
| 2010/0094116 A1* | 4/2010 | Silverstein ............ A61B 5/06 600/409 |
| 2010/0137944 A1 | 6/2010 | Zhu |
| 2010/0137955 A1 | 6/2010 | Milijasevic et al. |
| 2010/0152538 A1* | 6/2010 | Gleason ............ A61B 1/00055 600/117 |
| 2010/0204569 A1 | 8/2010 | Burnside et al. |
| 2010/0211135 A1 | 8/2010 | Caparso et al. |
| 2010/0222844 A1 | 9/2010 | Troosters et al. |
| 2010/0267265 A1 | 10/2010 | Dilmaghanian |
| 2010/0274312 A1 | 10/2010 | Alataris et al. |
| 2010/0274314 A1 | 10/2010 | Alataris et al. |
| 2010/0274315 A1 | 10/2010 | Alataris et al. |
| 2010/0274316 A1 | 10/2010 | Alataris et al. |
| 2010/0274336 A1 | 10/2010 | Nguyen-Stella et al. |
| 2010/0286551 A1 | 11/2010 | Harlev et al. |
| 2010/0298905 A1 | 11/2010 | Simon |
| 2010/0305631 A1 | 12/2010 | Bradley et al. |

(56) References Cited

U.S. PATENT DOCUMENTS

| | | |
|---|---|---|
| 2010/0324414 A1 | 12/2010 | Harlev et al. |
| 2010/0324570 A1 | 12/2010 | Rooney et al. |
| 2011/0009927 A1 | 1/2011 | Parker et al. |
| 2011/0031961 A1 | 2/2011 | Durand et al. |
| 2011/0046617 A1 | 2/2011 | Thompson et al. |
| 2011/0054304 A1* | 3/2011 | Markowitz ............ A61B 34/20 600/424 |
| 2011/0054551 A1 | 3/2011 | Zhu et al. |
| 2011/0060386 A1 | 3/2011 | Woods et al. |
| 2011/0066407 A1 | 3/2011 | Butson et al. |
| 2011/0093051 A1 | 4/2011 | Davis |
| 2011/0106052 A1 | 5/2011 | Chiang et al. |
| 2011/0160568 A1* | 6/2011 | Seeley ................... A61B 34/20 600/424 |
| 2011/0178573 A1 | 7/2011 | Nguyen-Stella et al. |
| 2011/0245903 A1 | 10/2011 | Schulte et al. |
| 2011/0307032 A1 | 12/2011 | Goetz et al. |
| 2012/0083709 A1 | 4/2012 | Parker et al. |
| 2012/0083856 A1 | 4/2012 | Thacker et al. |
| 2012/0083857 A1 | 4/2012 | Bradley |
| 2012/0173946 A1 | 7/2012 | Terry et al. |
| 2012/0232626 A1 | 9/2012 | Daglow |
| 2012/0232810 A1 | 9/2012 | Kaipio et al. |
| 2013/0066411 A1 | 3/2013 | Thacker et al. |
| 2013/0096642 A1 | 4/2013 | Wingeier |
| 2013/0116754 A1 | 5/2013 | Sharma et al. |
| 2013/0261697 A1 | 10/2013 | Parker |
| 2014/0303685 A1 | 10/2014 | Rosenberg et al. |
| 2015/0012077 A1 | 1/2015 | Parker et al. |
| 2016/0059006 A1 | 3/2016 | Doan et al. |
| 2016/0302827 A1 | 10/2016 | Chitre |
| 2016/0354609 A1 | 12/2016 | Parker et al. |
| 2016/0360993 A1 | 12/2016 | Thacker et al. |
| 2019/0217096 A1 | 7/2019 | Parker |

FOREIGN PATENT DOCUMENTS

| | | |
|---|---|---|
| WO | WO-9003824 A1 | 4/1990 |
| WO | WO-2009097224 A1 | 8/2009 |
| WO | WO-2009129329 A1 | 10/2009 |
| WO | WO-2011014570 A1 | 2/2011 |
| WO | WO-2011143258 | 11/2011 |

OTHER PUBLICATIONS

Kulkarni et al., "A two-layered forward model of tissue for electrical; impedance tomography," Physiol Meas., 30(6); pp. 1-24, Jun. 2009.

Medtronic "N'Vision Cliniciam (8840) Programmer with Software (8870)—Restore and RestorePRIME Neurostimulation Systems for Pain," 2006, 109 pages.

Falowski et al. "Spinal Cord Stimulation: An Update," Neurotherapeutics: The Journal of the American Society for Experimental NeuroTherapeutics, vol. 5, Jan. 2008, 14 pages.

Shealy et al., "Electrical Inhibition of Pain: Experimental Evaluation," Anesthesia and Analgesia, vol. 46, No. 3, May-Jun. 1967, 7 pages.

* cited by examiner

SYSTEMS AND METHODS FOR POSITIONING IMPLANTED DEVICES IN A PATIENT

CROSS-REFERENCE TO RELATED APPLICATIONS

This application is a continuation of U.S. patent application Ser. No. 15/148,987, filed May 6, 2016, which is a continuation of U.S. patent application Ser. No. 14/598,114, now issued as U.S. Pat. No. 9,345,891, filed Jan. 15, 2015, which is a continuation of U.S. patent application Ser. No. 12/895,403, now issued as U.S. Pat. No. 8,965,482, filed Sep. 30, 2010, which are incorporated herein by reference in their entireties.

TECHNICAL HELD

The present technology is directed generally to systems and methods for positioning implanted devices in a patient.

BACKGROUND

Neurological stimulators have been developed to treat pain, movement disorders, functional disorders, spasticity, cancer, cardiac disorders, and various other medical conditions. Implantable neurological stimulation systems generally have an implantable pulse generator and one or more leads that deliver electrical pulses to neurological tissue or muscle tissue. For example, several neurological stimulation systems for spinal cord stimulation (SCS) have cylindrical leads that include a lead body with a circular cross-sectional shape and multiple conductive rings spaced apart from each other at the distal end of the lead body. The conductive rings operate as individual electrodes and the SCS leads are typically implanted either surgically or percutaneously through a large needle inserted into the epidural space, with or without the assistance of a stylet.

Once implanted, the pulse generator applies electrical pulses to the electrodes, which in turn modify the function of the patient's nervous system, such as by altering the patient's responsiveness to sensory stimuli and/or altering the patient's motor-circuit output. During pain treatment, the pulse generator applies electrical pulses to the electrodes, which in turn can generate sensations that mask or otherwise alter the patient's sensation of pain. For example, in many cases, patients report a tingling or paresthesia that is perceived as more pleasant and/or less uncomfortable than the underlying pain sensation. In other cases, the patients can report pain relief without paresthesia or other sensations.

In any of the foregoing systems, it is important for the practitioner to accurately position the stimulator in order to provide effective therapy. One approach to accurately positioning the stimulator is to implant the stimulator in a surgical procedure so that the practitioner has a clear visual access to the implantation site. However, many patients and practitioners wish to avoid the invasiveness and associated likelihood for complications typical of a surgical procedure. Accordingly, many patients and practitioners prefer a less invasive (e.g., percutaneous) implantation technique. With a percutaneous approach, the practitioner typically is unable to see exactly where the device is positioned because the device is beneath the patient's skin and in most SCS cases, within the patient's spinal column. In addition, the process typically requires the patient to provide feedback to the practitioner based on that patient's sensations. Accordingly, the industry has developed a variety of techniques for visualizing medical devices and anatomical features below the patient's skin as the device is implanted. Such techniques include fluoroscopy, which is commonly used to aid the practitioner when implanting SCS leads. However, a drawback with fluoroscopy is that it results in added expense to the SCS implantation procedure, it may be cumbersome to implement, it limits the implantation procedure to sites with fluoroscopy equipment, and it exposes the patient to unwanted x-ray radiation. Accordingly, there remains a need in the art for improved visualization techniques that can be used to implant patient devices with greater ease, accuracy, and lower cost.

DETAILED DESCRIPTION

The present technology is directed generally to systems and methods for positioning implanted devices in a patient. In at least some contexts, the systems and methods are used to implant leads proximate to the patient's spinal cord to deliver high frequency signals that modulate neural activity at the patient's spine, in particular embodiments, to address chronic pain. In other embodiments, however, the systems and associated methods can have different configurations, components, and/or procedures. Still other embodiments may eliminate particular components or procedures. A person of ordinary skill in the relevant art, therefore, will understand that the present technology may include other embodiments with additional elements, and/or may include other embodiments without several of the features shown and described below with reference to FIGS. 1A-7D.

Several aspects of the technology are embodied in computing devices, e.g., programmed pulse generators, controllers and/or other devices. The computing devices on which the described technology can be implemented may include one or more central processing units, memory, input devices (e.g., input ports), output devices (e.g., display devices), storage devices, and network devices (e.g., network interfaces). The memory and storage devices are computer-readable media that may store instructions that implement the technology. In many embodiments, the computer readable media are tangible media. In other embodiments, the data structures and message structures may be stored or transmitted via an intangible data transmission medium, such as a signal on a communications link. Various suitable communications links may be used, including but not limited to a local area network and/or a wide-area network.

Figure 1A:
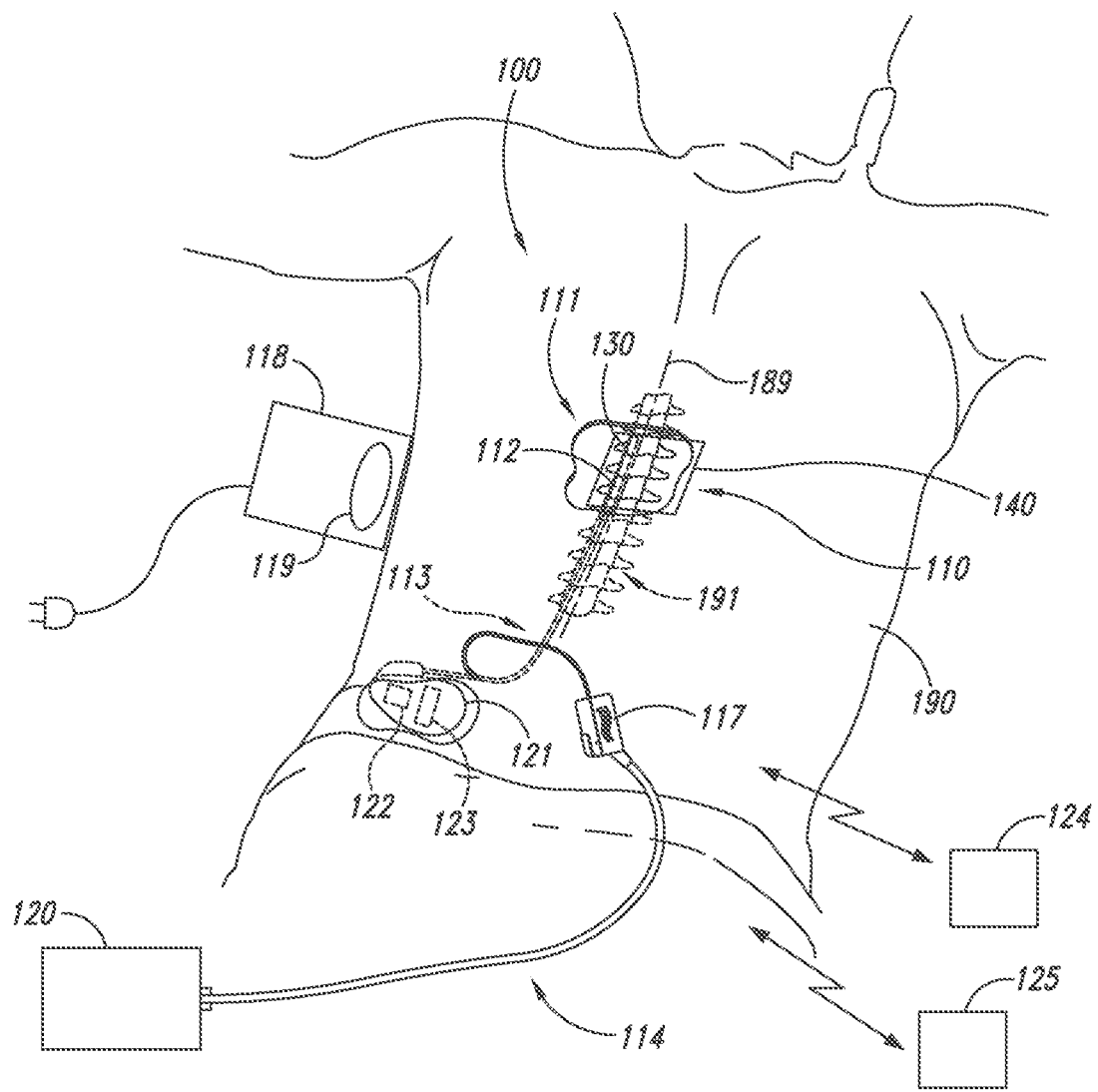
FIG. 1A is a partially schematic illustration of an implantable spinal cord modulation system positioned at a patient's spine to deliver therapeutic signals in accordance with several embodiments of the present disclosure.

FIG. 1A schematically illustrates a representative patient system 100 for providing relief from chronic pain and/or other conditions, arranged relative to the general anatomy of a patient's spinal cord 191. The overall patient system 100 can include a signal delivery system 110, which may be implanted within a patient 190, typically at or near the patient's midline 189, and coupled to a pulse generator 121. The signal delivery system 110 can provide therapeutic electrical signals to the patient during operation. The overall patient system 100 can further include a signal transmission system 130 and a signal detector system 140. The signals handled by the signal transmission system 130 and the signal detector system 140 can function primarily to identify the location of the signal delivery system 110, rather than to provide therapy to the patient. Accordingly, the signal transmission system 130 and signal detector system 140 can operate independently of the signal delivery system 110 to guide the practitioner as he/she positions elements of the signal delivery system 110 within the patient. Nevertheless, in particular embodiments, certain elements of the signal transmission system 130 can be shared with the signal delivery system 110. Aspects of the signal delivery system 110 are described immediately below, followed by a description of the signal transmission system 130 and the signal detector system 140.

In a representative example, the signal delivery system 110 includes a signal delivery device 111 that carries features for delivering therapy to the patient 190 after implantation. The pulse generator 121 can be connected directly to the signal delivery device 111, or it can be coupled to the signal delivery device 111 via a signal link 113 (e.g., an extension). In a further representative embodiment, the signal delivery device 111 can include an elongated lead or lead body 112. As used herein, the terms "lead" and "lead body" include any of a number of suitable substrates and/or support members that carry devices for providing therapy signals to the patient 190. For example, the lead 112 can include one or more electrodes or electrical contacts that direct electrical signals into the patient's tissue, such as to provide for patient relief. In other embodiments, the signal delivery device 111 can include structures other than a lead body (e.g., a paddle) that also direct electrical signals and/or other types of signals to the patient 190.

The pulse generator 121 can transmit signals (e.g., electrical signals) to the signal delivery device 111 that up-regulate (e.g., stimulate or excite) and/or down-regulate (e.g., block or suppress) target nerves. As used herein, and unless otherwise noted, the terms "modulate" and "modulation" refer generally to signals that have either type of the foregoing effects on the target nerves. The pulse generator 121 can include a machine-readable (e.g., computer-readable) medium containing instructions for generating and transmitting suitable therapy signals. The pulse generator 121 and/or other elements of the system 100 can include one or more processors 122, memories 123 and/or input/output devices. Accordingly, the process of providing modulation signals, providing guidance information for locating the signal delivery device 111, and/or executing other associated functions can be performed by computer-executable instructions contained by computer-readable media located at the pulse generator 121 and/or other system components. The pulse generator 121 can include multiple portions, elements, and/or subsystems (e.g., for directing signals in accordance with multiple signal delivery parameters), carried in a single housing, as shown in FIG. 1A, or in multiple housings.

In some embodiments, the pulse generator 121 can obtain power to generate the therapy signals from an external power source 118. The external power source 118 can transmit power to the implanted pulse generator 121 using electromagnetic induction (e.g., RF signals). For example, the external power source 118 can include an external coil 119 that communicates with a corresponding internal coil (not shown) within the implantable pulse generator 121. The external power source 118 can be portable for ease of use.

During at least some procedures, an external programmer 120 (e.g., a trial modulator) can be coupled to the signal delivery device 111 during an initial procedure, prior to implanting the pulse generator 121. For example, a practitioner (e.g., a physician and/or a company representative) can use the external programmer 120 to vary the modulation parameters provided to the signal delivery device 111 in real time, and select optimal or particularly efficacious parameters. These parameters can include the location from which the electrical signals are emitted, as well as the characteristics of the electrical signals provided to the signal delivery device 111. In a typical process, the practitioner uses a cable assembly 114 to temporarily connect the external programmer 120 to the signal delivery device 111. The practitioner can test the efficacy of the signal delivery device 111 in an initial position. The practitioner can then disconnect the cable assembly 114 (e.g., at a connector 117), reposition the signal delivery device 111, and reapply the electrical modulation. This process can be performed iteratively until the practitioner obtains the desired position for the signal delivery device 111. Optionally, the practitioner may move the partially implanted signal delivery element 111 without disconnecting the cable assembly 114.

After a trial period with the external programmer 120, the practitioner can implant the implantable pulse generator 121 within the patient 190 for longer term treatment. The signal delivery parameters provided by the pulse generator 121 can still be updated after the pulse generator 121 is implanted, via a wireless physician's programmer 125 (e.g., a physician's remote) and/or a wireless patient programmer 124 (e.g., a patient remote). Generally, the patient 190 has control over fewer parameters than does the practitioner.

Figure 1B:
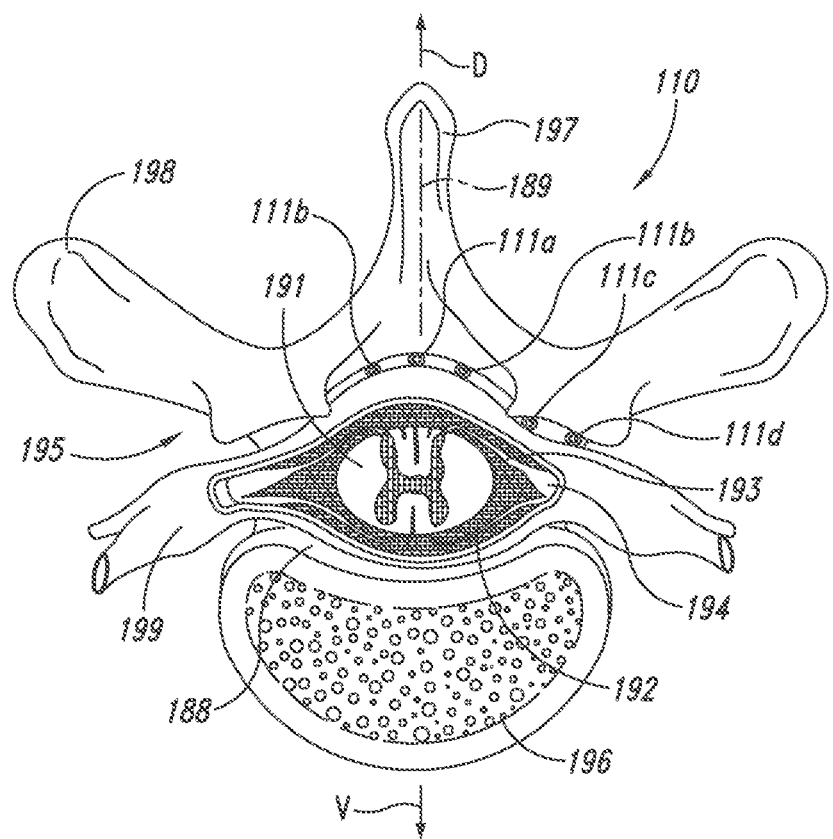
FIG. 1B is a partially schematic, cross-sectional illustration of a patient's spine, illustrating representative locations for an implanted lead in accordance with an embodiment of the disclosure.

FIG. 1B is a cross-sectional illustration of the spinal cord 191 and an adjacent vertebra 195 (based generally on information from Crossman and Neary, "Neuroanatomy," 1995 (published by Churchill Livingstone)), along with multiple signal delivery devices 111 (shown as signal delivery devices 111a-d) implanted at representative locations. For purposes of illustration, multiple signal delivery devices 111 are shown in FIG. 1B implanted in a single patient. In actual use, any given patient will likely receive fewer than all the signal delivery devices 111 shown in FIG. 1B.

The spinal cord 191 is situated within a vertebral foramen 188, between a ventrally located ventral body 196 and a dorsally located transverse process 198 and spinous process 197. Arrows V and D identify the ventral and dorsal directions, respectively. The spinal cord 191 itself is located within the dura mater 199, which also surrounds portions of the nerves exiting the spinal cord 191, including the ventral roots 192, dorsal roots 193 and dorsal root ganglia 194. In one embodiment, a single first signal delivery device 111*a* is positioned within the vertebral foramen 188, at or approximately at the spinal cord midline 189. In another embodiment, two second signal delivery devices 111*b* are positioned just off the spinal cord midline 189 (e.g., about 1 mm. offset) in opposing lateral directions so that the two signal delivery devices 111*b* are spaced apart from each other by about 2 mm. In still further embodiments, a single signal delivery device or pairs of signal delivery devices can be positioned at other locations, e.g., at the dorsal root entry zone as shown by a third signal delivery device 111*c*, or at the dorsal root ganglia 194, as shown by a fourth signal delivery device 111*d*.

In any of the foregoing embodiments, it is important that the signal delivery device 111 be placed at a target location that is expected (e.g., by a practitioner) to produce efficacious results in the patient when activated. The following disclosure describes techniques and systems for improving the level of accuracy with which the devices are positioned.

Figure 2:
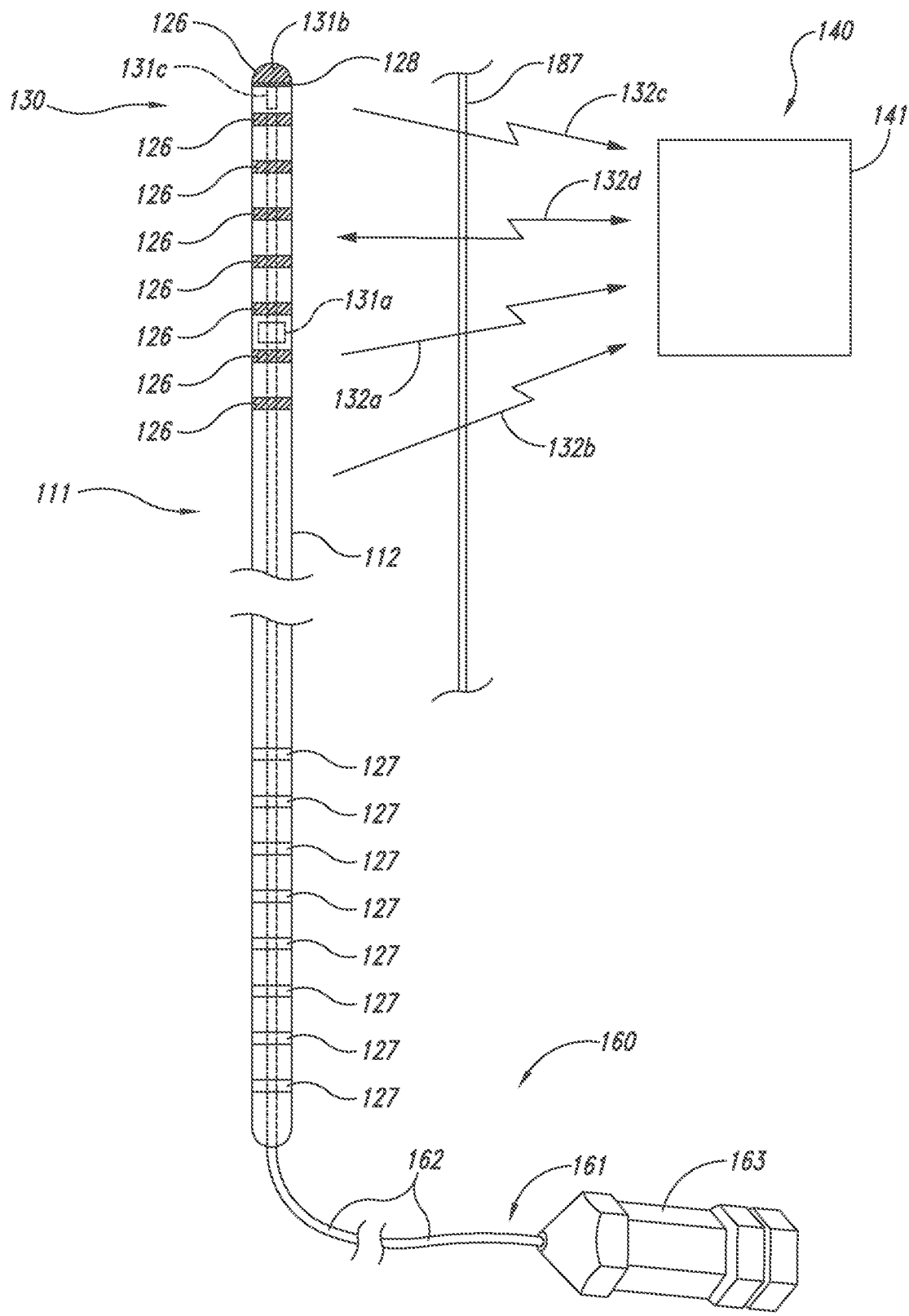
FIG. 2 is a partially schematic illustration of a representative signal delivery device, signal transmission device, and signal detection device, configured in accordance with an embodiment of the disclosure.

FIG. 2 is a partially schematic illustration of a representative signal delivery device 111 that includes a lead 112 carrying a plurality of ring-shaped therapy contacts 126 positioned toward a distal end to deliver a therapy signal to the patient when the lead 112 is implanted. The lead 112 includes internal wires (not visible in FIG. 2) that extend between the therapy contacts 126 at the distal end of the lead 112, and corresponding connection contacts 127 positioned at the lead proximal end. After implantation, the connection contacts 127 are connected to the external programmer 120 or the implanted pulse generator 121 discussed above with reference to FIG. 1A. During implantation, an implanting tool 160 (e.g., a stylet 161) is temporarily coupled to the lead 112 to support the lead 112 as it is inserted into the patient. For example, the implanting tool 160 can include a shaft 162 that is slideably and releasably inserted (via, e.g., a handle 163) into an axially-extending opening in the lead 112. The shaft 162 is generally flexible, but more rigid than the lead 112 to allow the practitioner to insert the lead 112 and control its position during implantation. A stylet stop 128 at the distal end of the lead opening prevents the practitioner from over-inserting the stylet shaft 162.

The lead 112 and/or other portions of the overall system 100 can include features that guide the practitioner when positioning the lead 112 at a target location. For example, the signal transmission system 130 can be carried by the lead 112 and/or the implanting tool 160, and can communicate with the signal detector system 140 located outside the patient's body. In a particular embodiment, the signal transmission system 130 includes one or more signal transmission devices 131. For purposes of illustration, several different signal transmission devices 131 are shown together in FIG. 2 as first, second and third signal transmission devices 131*a*, 131*b*, 131*c*, though in most embodiments, a single or single type of signal transmission device 131 will be implemented. The signal transmission devices 131 communicate with the signal detector system 140 via corresponding locator signals 132 (shown schematically as first, second and third locator signals 132*a*-132*c*). The signal transmission devices 131 can generate, emit, and/or reflect the locator signals 132 in a manner that is detected by a signal detector device 141 of the signal detector system 140. The first signal transmission device 131*a* can be carried by the lead 112, and can be independent of (e.g., electrically isolated from) the therapy contacts 126. The second signal transmission device 131*b* can also be carried by the lead 112, but can double as one of the therapy contacts 126. In a particular aspect of this embodiment, the second signal transmission device 131*b* doubles as the distal-most therapy contact 126, located at or near the distal tip of the lead 112. In other embodiments, the second signal transmission device 131*b* can double as any of the other therapy contacts 126. The third signal transmission device 131*c* is carried by the implanting tool 160, rather than the lead 112. For example, the third signal transmission device 131*c* can be located at the distal-most tip of the implanting tool 160.

An advantageous feature of the first signal transmission device 131*a* is that its independence of therapy contacts 126 frees it from being limited by the particular geometry and arrangement of the therapy contacts 126, which are typically sized, configured and arranged to provide optimal or highly effective and efficient therapy (e.g., modulation) signals. Instead, the first signal transmission device 131*a* can be tailored to provide effective and efficient first locator signals 132*a*, e.g., in cases where the locator signals differ significantly from the therapy/modulation signals. Conversely, an advantage of combining the functions of the second signal transmission device 131*b* with one of the therapy contacts 126 is that it reduces the need for an additional element in the overall patient system 100. An advantage of the third signal transmission device 131*c* is that it can be removed from the patient's body when it is no longer needed for locating the lead 112. Although the configuration and individual features of the three signal transmission devices 131*a*, 131*b*, and 131*c* in the embodiment of FIG. 2 affords unique advantages, signal transmission system 130 may comprise only a single or single type of signal transmission device 131, two such devices or types of devices 131, or more than three such devices or types of devices 131 in any combination of locations, configurations, and types as herein described.

The locator signals 132 transmitted by the signal transmission device 131 can have any of a variety of characteristics suitable for conveying location information wirelessly through the patient's skin 187 to the signal detector device 141. For example, in a particular embodiment, the locator signal 132 can include a radio frequency (RF) signal having a frequency in the range of from about 10 kHz to about 30 GHz. In other embodiments, the frequency of the locator signal 132 is outside the foregoing range. In still further embodiments, the signal transmission device 131 can be a magnetic device (e.g., a permanent magnet and/or an electromagnet) and can accordingly transmit locator signals 132 by virtue of magnetic fields, which are detected by the signal detector device 141. Accordingly, the term "locator signal" as used herein includes a wide variety of electromagnetic fields and transmissions that can be received or otherwise detected by an appropriate detector device 141. The signal can be generally constant, as in the case of a magnetic field produced by a permanent magnet, or varying, as in the case of an RF signal. In still a further embodiment, the locator signal 132 can be an acoustic signal (e.g., ultrasound) that is transmitted by the signal transmission device 131 and received by the signal detector device 141. In yet another aspect of this embodiment, the locator signal can actually be emitted from a location external to the patient's body, and the signal detector device 141 can receive or detect an echo or return signal, as indicated by fourth (two-way) locator signals 132*d*. Accordingly, unless otherwise indicated, the term "signal transmission device" includes devices that emit (e.g., actively generate) signals, and devices that reflect signals, with both types of signals selected to be detected by the signal detector device 141.

When the signal includes a reflected ultrasound signal, the signal emitter can be co-housed with the signal detector 141 to simplify use. The signal delivery device 111 and/or the implanting tool 160 can be constructed from materials specifically selected to be highly reflective to ultrasound signals and/or surface treatments to optimize ultrasound reflectivity. Materials having densities different than the densities of the adjacent tissue (which has a significant water content) typically have a higher acoustic impedance and accordingly generate reflections that can be readily distinguished from those produced by the adjacent tissue. Such materials can include polymers such as polyethylene or polyurethane. In other embodiments, the materials can include compositions having higher densities and/or materials that are also radiopaque, so that they can be used with a fluoroscopic detection technique and/or an ultrasonic detection technique. Suitable materials include platinum, iridium, tantalum, titanium and/or alloys of the foregoing materials. The materials can be applied to one or more of several elements of the signal delivery system 110, including the therapy contacts 126, the stylet stop 128, and/or the end of the stylet shaft 162, which can have a ball shape (e.g., a welded ball) to inhibit penetration into the distal end of the lead 112. In other embodiments, a radiopaque and acoustically reflective ink or other coating can be applied to any of the foregoing elements and/or to the outer surface of the stylet shaft 162 and/or to the outer surface of the lead 112. Suitable materials include radiopaque inks available from CJ Medical of Norton, Mass., and sputtered tantalum available from Isoflex Biomed of Rochester, N.Y.

In any of the foregoing embodiments, locator signals are generally transmitted (e.g., actively or by reflection) from the signal transmission device 131 to the signal detector device 141. As discussed above, signals can travel in both directions when the detected signal is a reflected signal. In other embodiments, the signal detector device 141 can transmit additional signals to the signal transmission device 131, e.g., to power the signal transmission device 131, and/or to query the signal transmission device 131 for additional information.

Figure 3:
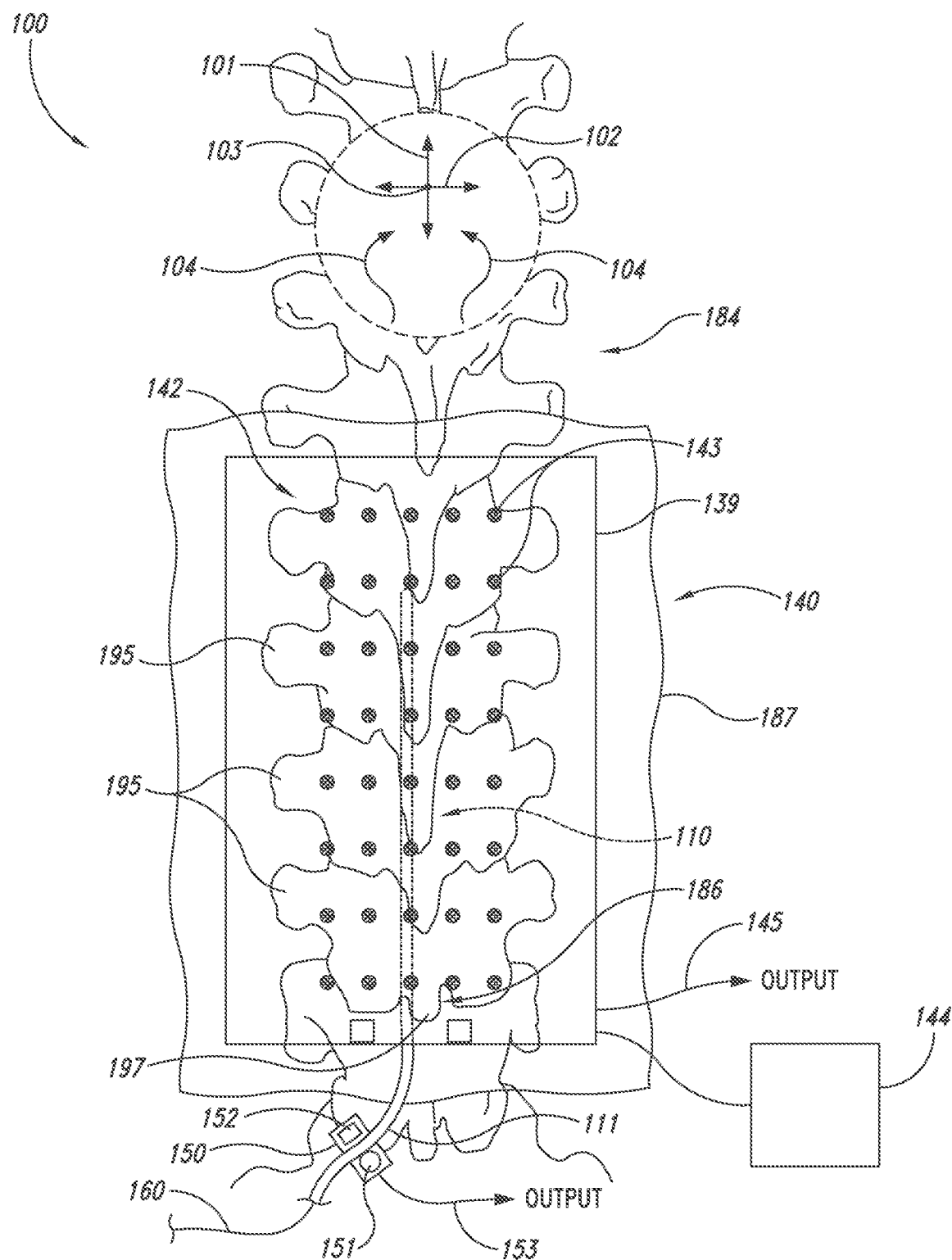
FIG. 3 is a partially schematic illustration of a signal detector system positioned over the patient's spine in accordance with an embodiment of the disclosure.

In at least some embodiments, the signal detector system 140 can include a single detector device 141, as shown in FIG. 2. In other embodiments (for example, as illustrated in FIG. 3), the signal detector system 140 can include an array 142 or other plurality of detector devices or elements 143, with each detector element 143 capable of detecting and responding to a locator signal. In a particular embodiment, the array 142 is positioned on the patient's skin 187 over the patient's spine 184. Each detector element 143 can be individually placed on the patient's skin 187, or the array 142 can include a flexible support member 139 (e.g., a thin plastic or fabric member or single- or multi-layer plastic or fabric composite, etc.) in which all the detector elements 143 are incorporated or located. For example, if support member 139 is a multi-layer construction of fabric and/or plastic, some or all detector elements 143 may be incorporated between one or more layers thereof and/or affixed to one or both outer surfaces of support member 139. If support member 139 is a single layer of material, detector elements 143 may be affixed to one or both surfaces of member 139. The support member 139 can be releasably attached to the patient's skin 187, e.g., via an adhesive, straps, or another suitable, releasable attachment mechanism. The support member 139 can accordingly maintain a constant or generally constant spacing between neighboring detector elements 143 of the array 142. The array 142 can include one or more index markers 146 that allow the practitioner to locate the array 142 properly relative to the patient's anatomy. For example, the practitioner can palpate and/or visually identify an anatomic feature 186 of the patient (e.g., the spinous process 197 of a specific vertebra 195) and locate the one or more index markers 146 relative to the anatomic feature 186. The detector elements 143 can be coupled to a power source 144 that powers the detector elements 143, and the detector elements 143 can communicate information to other elements of the overall system 100 via a detector output 145.

As the practitioner inserts the signal delivery system 110 along the patient's spine 184, the signal delivery system 110 (e.g., the signal delivery device 111 and associated implanting tool 160) can move in several directions. For example, as shown in FIG. 3, the signal delivery system 110 can move axially (or in a rostral/caudal direction) as indicated by arrows 101, laterally as indicated by arrows 102 and/or in a direct ventral/dorsal direction 103 (viewed end-on in FIG. 3). The direct ventral/dorsal direction 103 corresponds to a direction directly toward or away from the spinal cord. In at least some cases, the lead may tend to migrate around the spinal cord in a spiral fashion, as indicated by arrows 104.

Because the detector elements 143 shown in the array 142 are positioned in a plane (e.g., a generally flat plane) that contains the axial and lateral axes 101, 102, the detector elements 143 tend to be most sensitive to the location of the signal delivery system 110 in these generally orthogonal directions. The detector elements 143 may not be as sensitive to motion along the ventral/dorsal axis 103, and/or motion of the signal delivery system 110 wrapping around the spinal cord. Accordingly, the overall system 100 can include other features that may supplement the information received from the detector elements 143. In a particular embodiment, the overall system 100 can include an insertion tracker 150 (shown schematically in FIG. 3) that tracks the length of the signal delivery device 111 that has been inserted into the patient. In a first embodiment, the insertion tracker 150 can include markings (e.g., a scale) on the signal delivery device 111 or on the implanting tool 160 that the practitioner observes to track the length of the signal delivery device 111 that has been inserted. In another embodiment, the insertion tracker 150 includes a wheel 151 or other suitable mechanical, electromechanical or electro-optic device that automatically determines the length of the signal delivery device 111 inserted into the patient. The inserted length can be presented at a display 152 and/or directed remotely via an output signal 153.

In operation, the information received by the detector elements 143 can be used to estimate a length of the signal delivery device 111 projected into the plane of the array 142. This estimated length can be compared to the length indicated by the insertion tracker 150, either by the practitioner, or in an automated manner by the overall system 100, based on the output signal 153. If the location of the signal delivery device 111 as indicated by the detector elements 143 corresponds to (e.g., is identical or nearly identical to) the inserted length of the signal delivery device 111 identified by the insertion tracker 150, then the signal delivery device 111 has not likely deviated significantly from a plane located just above the spinal cord. Alternatively, if the detector elements 143 indicate that the signal delivery device 111 is not progressing (or progressing slowly) in the lateral or axial directions, but the insertion tracker 150 indicates that the signal delivery device 111 is in fact progressing (or progressing quickly), this can indicate to the practitioner that the signal delivery device 111 is traveling out of the plane of the array 142, e.g., either penetrating toward or into the spinal cord, or wrapping around the spinal cord. Further aspects of this operation are described later with reference to FIG. 5.

Figure 4:
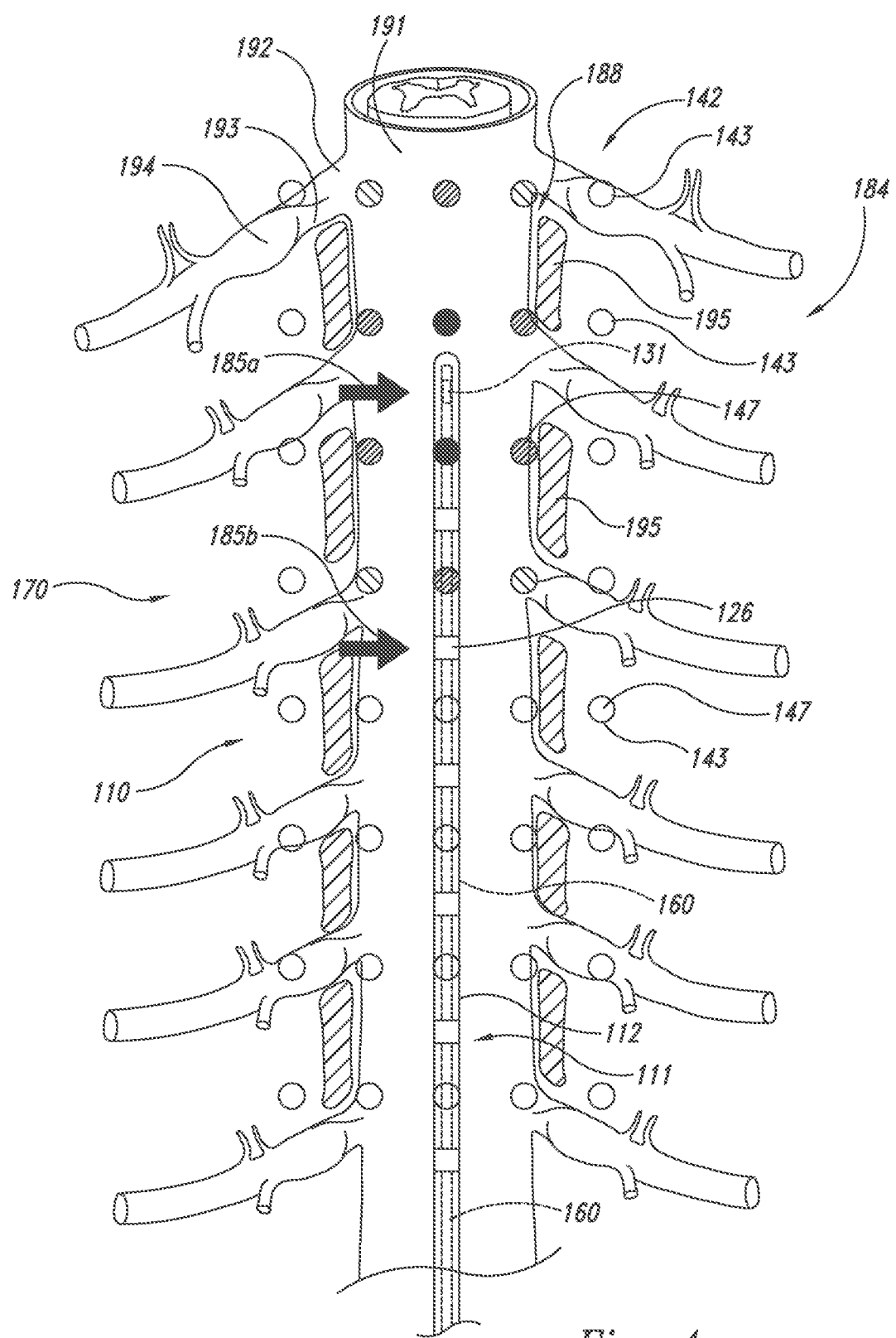
FIG. 4 is an enlarged illustration of a portion of the patient's spinal cord and a representative signal detector device.

FIG. 4 is a partially schematic illustration of the dorsal region of the patient's spinal cord 191, with the vertebrae 195 cut away (as shown in cross-section) and with the array 142 of detector elements 143 shown in position over the patient's spine 184. As discussed above, the array 142 is typically located on the patient's skin, external to the patient's body, but for purposes of clarity, the patient's skin is not shown in FIG. 4. In a particular aspect of this embodiment, the detector elements 143 present information corresponding to a characteristic of the detected locator signals, in addition to detecting/receiving the locator signals. For example, the detector elements 143 can each be co-located with a display element 147 and the display elements 143 together can form a display device 170. The display device 170 presents information corresponding to the strength of the signal received at individual detector elements 143. In one aspect of this embodiment, the individual display elements 147 include an LED or other light source that presents light to the practitioner having a characteristic indicating the signal strength detected at that location. For example, the light can be brighter at a location where the signal is stronger, and dimmer where the signal is weaker. In other embodiments, the light can have one color where the signal is strong and a different color where the signal is weak. In still other embodiments, the light can flash intermittently where the signal is weak and remain steady where the signal is strong (or vice-versa). Combinations of the foregoing characteristics of the light can also be used, with or without other features such as an aural signal indicative of a strong or weak signal. For purposes of illustration, light corresponding to strong signals is indicated in FIG. 4 with a heavier shading.

As shown in FIG. 4, the signal delivery device 111 has been advanced along the patient's spinal cord 191 via an implanting tool 160 that carries a signal transmission device 131 at its distal tip. Accordingly, the display elements 147 located closest to the signal transmission device 131 indicate the highest strength signal, and those further away from the signal transmission device 131 identify weaker signals. In some cases, the practitioner may position the signal delivery device 111 so that the signal transmission device 131 is aligned at a selected target location (e.g., a first target location 185a). In other cases, the target location (e.g., a second target location 185b) may be located apart from the signal emission device 131, for example, in cases for which the practitioner deliberately wishes to have a part of the signal delivery device 111 other than the distal-most tip aligned with the second target location 185b. In either embodiment, the practitioner can use the information presented by the display elements 147 to locate the signal transmission device 131 and, by knowing the relative spacing between the signal transmission device 131 and each of the therapy contacts 126, can locate any given therapy contact 126 with equal or generally equal accuracy.

Figure 5:
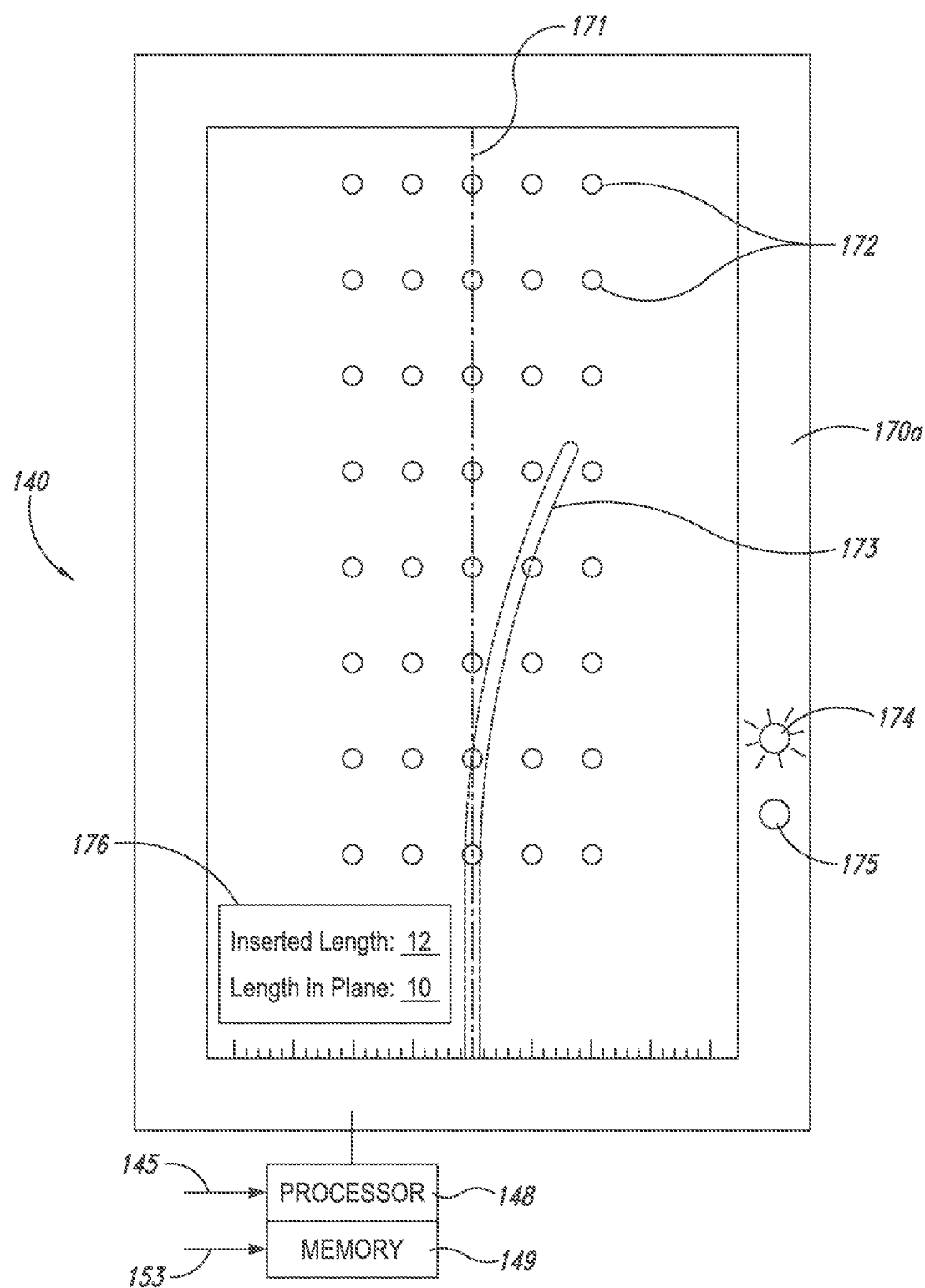
FIG. 5 is a schematic illustration of a signal detector system and display for presenting results obtained during procedures in accordance with embodiments of the disclosure.

In an embodiment shown in FIG. 4, the display elements 147 present information corresponding to the location of the signal transmission device 131 in situ, directly on the patient's skin overlying the spine. In other embodiments, this information can be presented at a remote location, in addition to, or in lieu of being presented in situ. For example, FIG. 5 illustrates a signal detector system 140 that displays information at a position spaced apart from the detector elements 143 (shown in FIG. 4). In a particular embodiment, the signal detector system 140 includes a processor 148 and a memory 149 that receive and store signal detector output 145 from the detector elements 143, and receive and store insertion tracker output 153 from the insertion tracker 150 (FIG. 4). This information is processed (e.g., via instructions contained by a computer-readable medium) and presented at a display device 170a, e.g., an LCD or LED screen. The display device 170a can include a graphical depiction of the patient's spinal cord midline via a midline indicator 171 and can graphically display detector element indicators 172 which are spaced apart from each other in a manner that corresponds to the spacing of the detector elements 143 on the patient's back. The detector element indicators 172 can be illuminated or otherwise presented in a manner that distinguishes strong detected signals from weaker detected signals, e.g, as previously described with respect to the embodiment of FIG. 4. In addition to or in lieu of presenting the detector element indicators 172, the display device 170a can present a signal delivery device indicator 173 that represents the location of the signal delivery device as determined by the signal detector system 140, based on the information received at the detector elements 143 (e.g., using a suitable interpolation scheme). Accordingly, the practitioner can view the display device 170a to obtain a graphical presentation of the location of the signal delivery device (which is not visible) relative to the patient's midline and the receiver elements 143 (which are visible).

The foregoing information received from the detector elements 143 can be combined with information received via the insertion tracker output 153 to indicate when the signal delivery device 111 (FIG. 4) moves out of plane. As discussed above, it is expected that the signal delivery device 111 will be out of plane when the lead length determined via the array 142 of detector elements 143 is less than the lead length determined by the insertion tracker 150. This information can be presented via an out-of-plane indicator 174 that illuminates when the lead is out of plane. This information can also be conveyed to the practitioner via an inserted length display 176 which compares the calculated length of the signal delivery device in the plane of the array 142, with the measured length of the signal delivery device actually inserted into the patient. The information presented at the display device 170a can still further include an intrathecal penetration indicator 175, which indicates that the dura around the spinal cord has been penetrated. Further information corresponding to this aspect of the system is described further below with reference to FIG. 6.

Figure 6:
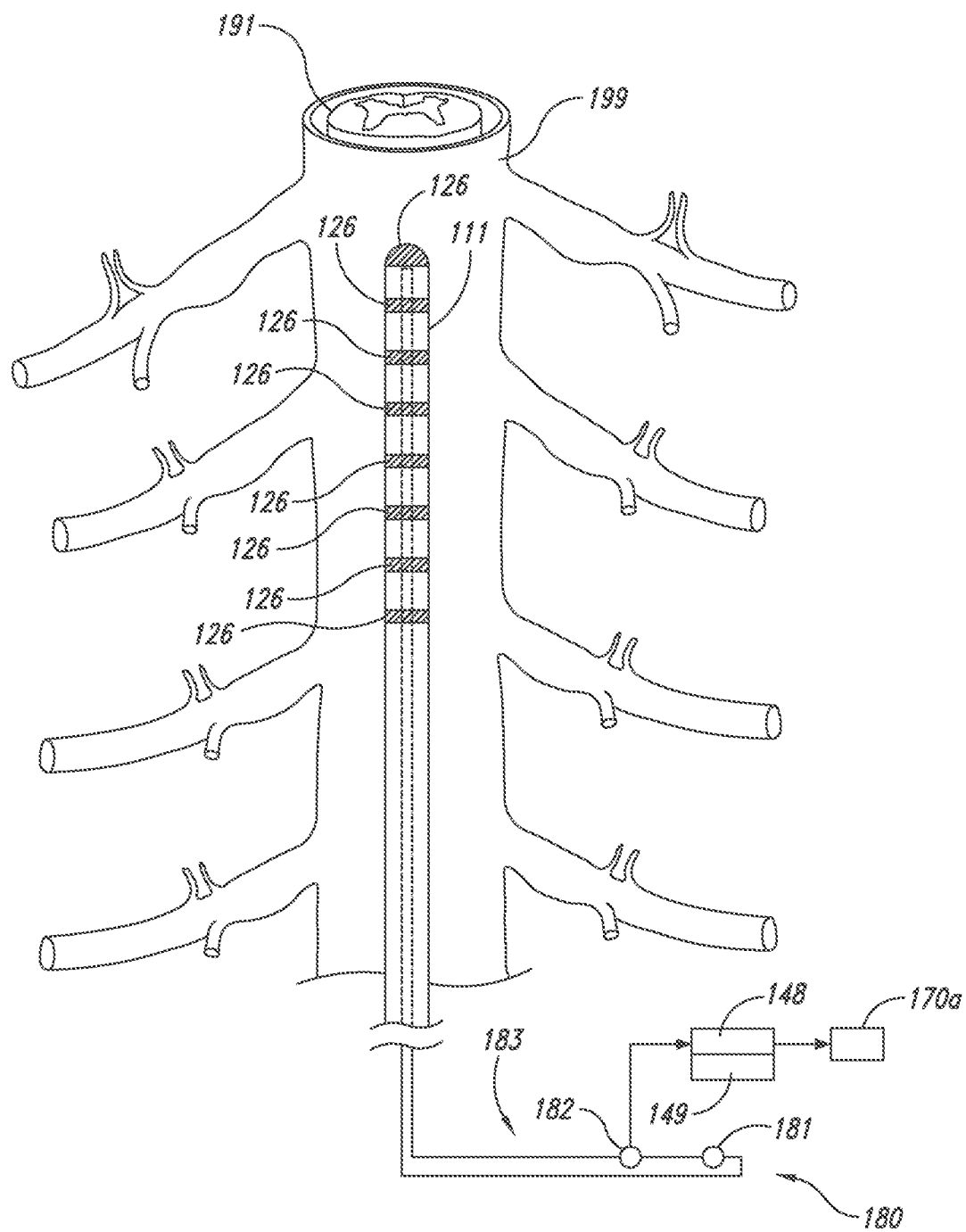
FIG. 6 is a schematic illustration of an intrathecal penetration detector configured in accordance with an embodiment of the disclosure.

FIG. 6 schematically illustrates an intrathecal penetration detector 180 that can be used alone or in conjunction with other features of the overall patient system 100 described above to aid the practitioner in identifying the location of the signal delivery device 111. The intrathecal penetration detector 180 take advantage of the low impedance that cerebral spinal fluid (CSF) has relative to the surrounding tissue in the spinal cord region. In particular, the intrathecal penetration detector 180 can use the impedance difference between CSF and the surrounding tissue to determine whether the dura 199 around the spinal cord 191 has been penetrated. In a particular embodiment, the intrathecal penetration detector 180 can detect an unexpectedly low impedance of a circuit that includes the signal delivery device 111 and the adjacent patient tissue, and identify this event to the practitioner as an indication that the signal delivery device 111 has potentially damaged or penetrated through the dura 199 of the patient's spinal cord 191. In most applications, it is undesirable to penetrate the dura 199 and therefore providing an indication of intrathecal penetration can allow the practitioner to withdraw and reposition the signal delivery device 111, optionally repair the damaged dura 199, and complete the process of implanting the signal delivery device 111.

In a particular embodiment, the intrathecal penetration detector 180 includes a power source 181 that applies a detection signal to a detection circuit 183. The detection circuit 183 includes patient tissue, and can further include one or more of the therapy contacts 126 in contact with the patient tissue. Using the therapy contacts 126 as part of the impedance circuit 183 reduces the need for adding additional features to the signal delivery device 111; nevertheless, in another embodiment, the signal delivery device 111 can carry contacts that are dedicated to impedance detection. In a particular embodiment, the detection circuit 183 can include two selected therapy contacts 126 and the patient tissue located between the two therapy contacts 126. In another embodiment, the detection circuit 183 can include a single therapy contact 126 and ground (e.g., a patient ground pad).

The intrathecal penetration detector 180 further includes an impedance detector 182 in the detection circuit 183 that identifies the impedance of the circuit 183. The impedance detector 182 can be connected to the processor 148, memory 149, and display device 170a described above with reference to FIG. 5 or to another processor and/or output device. In operation, the power source 181 provides a detection signal (e.g., a pulsed subthreshold signal with a current amplitude of about 0.2 milliamps, a pulse width of about 80 microseconds). The detection signal can be subthreshold to avoid inadvertently stimulating the patients' motor and/or sensory neural pathways. The pulses can be delivered in bursts at any suitable frequency, e.g., a frequency provided by the external programmer 120 (FIG. 1A). In a representative embodiment, the frequency can coincide with a representative therapy frequency (e.g., about 3 kHz to about 50 kHz) and in other embodiments, can have other values.

It is generally expected that the impedance of a circuit that includes two therapy contacts 126, as shown schematically in FIG. 6, will have an impedance of less than 1000 ohms, and typically an impedance in the range of about 300 ohms to about 600 ohms. If the impedance falls below a first threshold (e.g., about 200 ohms), the detector 180 and/or other elements of the system 100 can issue a warning, calling the practitioner's attention to the possibility of a CSF leak. If the impedance falls below a second threshold, e.g., about 50 ohms, the detector 180 and/or other elements of the system 100 can indicate a likely intrathecal penetration by the contact(s) 126a that are included in the detection circuit 183. As discussed above with reference to FIG. 5, this indication can be presented at the display device 170. In other embodiments, the indication can be presented in other manners, e.g., aurally. In still further embodiments, the foregoing threshold levels may have different values. For example, if the implant procedure includes using large amounts of saline, the "typical" impedance may fall from 300-600 ohms to 180 ohms, in which case the practitioner may require a lower threshold level (e.g., 150 ohms rather than 200 ohms) for an indication of CSF leakage. In other patients, e.g., patients with a significant amount of scar tissue, the "typical" impedance may be much larger than 1000 ohms, e.g., 200 ohms.

In a particular embodiment, the practitioner can select from any of the therapy contacts 126 to be included in the impedance detection circuit 183. In at least some embodiments, the practitioner may wish to include the distal-most therapy contact (e.g., at the distal tip of the signal delivery device 111) in the detection circuit 183 to provide an early indication that the signal delivery device 111 has penetrated the dura 199. If the signal delivery device 111 does not include a therapy contact 126 at the tip, a special-purpose contact can be added to the signal delivery device 111, or the practitioner can use the therapy contact 126 closest to the tip. In other embodiments, the practitioner may wish to include one or more of the other therapy contacts 126 in the circuit, for example, to identify the extent and/or rate of a cerebral spinal fluid leak, and/or for other diagnostic purposes.

As discussed above, the information received from the impedance detector 182 can be processed to indicate to the practitioner whether or not the dura 199 has been penetrated. The information can be provided in a fairly straightforward manner, e.g., by indicating either no intrathecal penetration or intrathecal penetration, optionally with an intermediate indication of likely CSF leakage. In other embodiments, the intrathecal penetration detector 180 can provide more sophisticated information. For example, the intrathecal penetration detector 180 can employ a multiplex arrangement or other suitable signal processing arrangement to scan over the therapy contacts 126 and identify issues or insipient issues associated with any of the contacts 126. The intrathecal penetration detector 180 can track a rate at which a drop in impedance passes along the signal delivery device 111 (e.g., as detected by multiple therapy contacts 126) to provide the practitioner with an indication of the rate at which CSF is leaking from the dura 199. In other embodiments, the intrathecal penetration detector 180 can include other arrangements. For example, the intrathecal penetration detector 180 can indicate which contacts(s) 126 have lower than expected associated impedance. In a particular example, the tip of the signal delivery device may penetrate the dura 199 by breaking the continuity of the dura 199 without actually proceeding into the subdural space. Leaking CSF may then be indicated by low impedances at proximal therapy contacts 126 as they pass by the break in the dura 199, and/or as CSF flows in a proximal direction, but a normal impedance (at least for a period of time) at the distalmost therapy contact 126.

Figure 7A:
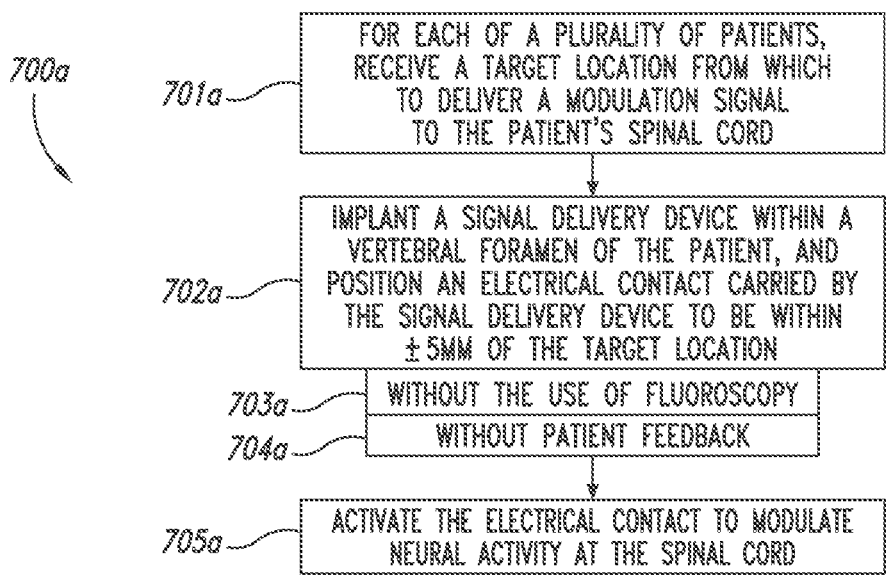
FIGS. 7A-7D illustrate processes for implanting patient devices in accordance with several embodiments of the disclosure.

FIGS. 7A-7D illustrate flow diagrams of methods in accordance with several embodiments of the disclosure described above. As described above, many of the steps in these methods may be performed automatically by instructions contained in one or more computer readable media. FIG. 7A illustrates a process 700a that includes, for each of a plurality of patients, receiving a target location from which to deliver a modulation signal to the patient's spinal cord (process portion 701a). The target location can be a single location or one of multiple locations, and can have axial and lateral coordinates selected to produce a desired patient effect. The process 700a can further include implanting a signal delivery device within a vertebral foramen of the patient, and positioning an electrical contact carried by the signal delivery device to be within ±5 mm. of the target location (process portion 702a). In particular embodiments, this accuracy level can be obtained in the axial and/or lateral directions via a single signal detector or via an array of detector elements. The same level of accuracy can be obtained in the dorsal/ventral direction, e.g., via an insertion tracker or other suitable methodology.

The foregoing process can be performed without the use of fluoroscopy (process portion 703a). For example, in particular embodiments, the practitioner can use electromagnetic techniques (e.g., RF or magnetic techniques) or ultrasound techniques to accurately implant the signal delivery device on a consistent, repeatable basis over multiple patients (e.g., a patient population numbering in the tens or hundreds or more). In further particular embodiments, the accuracy of this method can be better than ±5 mm., e.g., ±2 mm. or ±1 mm., depending on factors that include, but are not limited to, the sensitivity of the signal detector or signal detector elements, the unidirectionality of the signal transmitters, and the spacing between signal detector elements. In any of these embodiments, the ability to locate the signal delivery device within the foregoing ranges without the use of fluoroscopy can simplify the implanting process, and can reduce the patient's exposure to x-ray radiation. In addition, fluoroscopy devices can be cumbersome and, due to the protective gear worn by the practitioner, can interfere with the practitioners freedom of movement. Still further, fluoroscopy equipment is generally expensive and not generally available in remote and/or developing parts of the world. The current technology can reduce or eliminate the dependence on fluoroscopy for accurate device placement which can in turn allow the device and associated therapy to be used in a larger number of treatment centers (i.e., those without fluoroscopic equipment) and a concomitant potentially greater number of patients in need of such therapy.

Optionally, the process 700a can be performed with less or no patient feedback (process portion 704a). For example, the increased accuracy with which the signal delivery device is implanted in the first instance can reduce the number of subsequent iterations the practitioner and patient engage in to identify an effective location for the signal delivery device and associated therapy contacts. Such iterations can include moving the signal delivery device and/or selecting different active contacts on the signal delivery device.

Once the signal delivery device is implanted, it can be activated to modulate neural activity at the spinal cord (process portion 705a). In a particular embodiment, the therapy includes RF signals delivered to the patient's spinal cord at a frequency of from about 3 kHz to about 50 kHz to address patient pain. Further details of suitable signal delivery parameters are included in pending U.S. patent application Ser. No. 12/765,747, filed on Apr. 22, 2010 and incorporated herein by reference in its entirety. In other embodiments, the signal delivery device can provide signals in accordance with other signal delivery parameters to treat the same or other patient indications, at the same or other implantation sites.

Figure 7B:
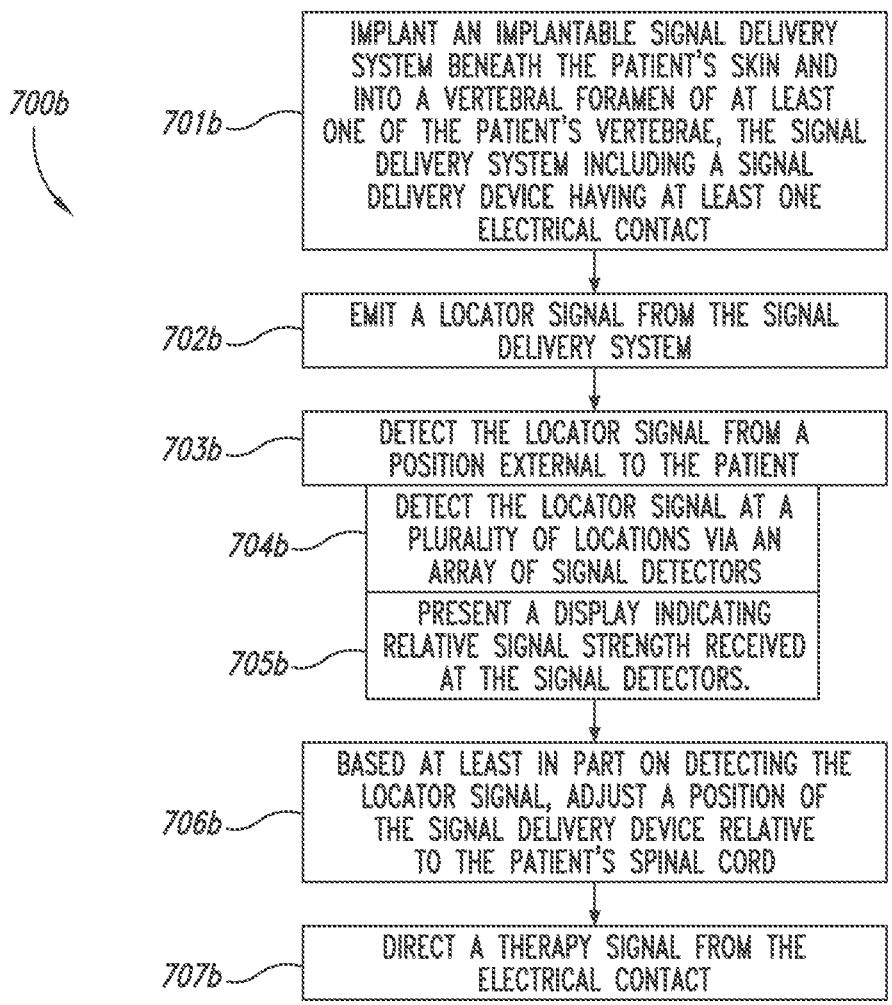

FIG. 7B is a flow diagram illustrating a process 700b in accordance with another embodiment of the disclosure, which includes implanting an implantable signal delivery system beneath the patient's skin and into a vertebral foramen of at least one of the patient's vertebrae (process portion 701b). The signal delivery system includes a signal delivery device having at least one electrical contact. In process portion 702b, a locator signal is emitted from the signal delivery system. As discussed above, the locator signal can be emitted from the signal delivery device and/or from an implanting tool that temporarily carries the signal delivery device during an implanting process. In process portion 703b, the locator signal is detected from a position external to the patient. In particular embodiments, the locator signal can be detected at a plurality of locations via an array of signal detectors (process portion 704b). In such embodiments, the results can be presented at a display indicating the relative signal strength received at the signal detectors (process portion 705b). Based at least in part on detecting the locator signal, the practitioner can adjust a position of the signal delivery device relative to the patient's spinal cord (process portion 706b) and the practitioner can then direct a therapy signal from the electrical contact (process portion 707b). As discussed above, an advantage of methods performed in accordance with the flow diagram shown in FIG. 7B is that they can allow the practitioner to accurately position the signal delivery device, e.g., without using fluoroscopy.

Figure 7C:
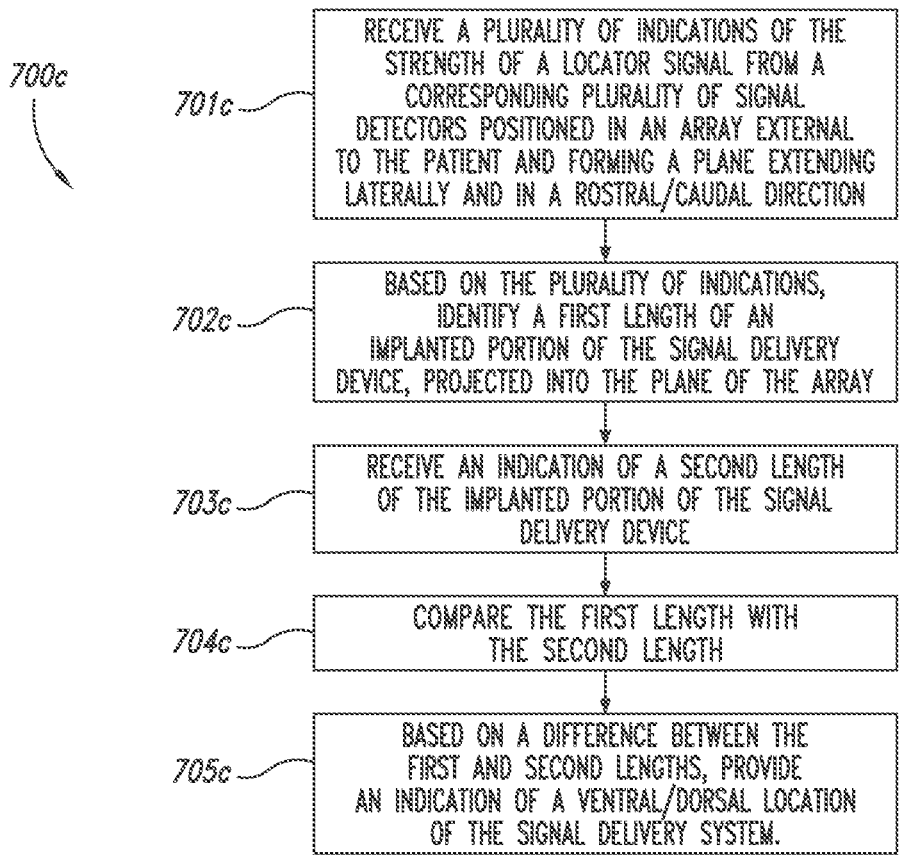

FIG. 7C illustrates another process 700c in accordance with an embodiment of the disclosure that includes receiving a plurality of indications of the strength of a locator signal from a corresponding plurality of signals detectors (process portion 701c). The signal detectors are positioned in an array external to the patient to form a plane extending laterally and in a rostral/caudal direction (e.g., an axial direction). In process portion 702c, a first length (e.g., a projected length of an implanted portion of the signal delivery device in the plane of the array) is identified, based upon the plurality of indications received in process portion 701c. In process portion 703c, an indication of the second length (e.g., an actual length) of the implanted portion of the signal delivery device is received. For example, process portion 703c can include receiving an indication of the actual implanted length via the insertion tracker discussed above with reference to FIG. 6. In process portion 704c, the second length of the implanted portion of the lead is compared with the first length and, based on a difference between the actual length and the projected length, an indication of a ventral/dorsal location of the signal delivery system is provided. For example, if the actual and projected lengths differ by more than a threshold amount (e.g., one mm. in one embodiment and other values in other embodiments), the foregoing indication can be triggered. The foregoing arrangement can be used to account for the fact that the signal delivery device may move along three different axes, while the detector array is positioned in, or generally in, a two-dimensional plane.

Figure 7D:
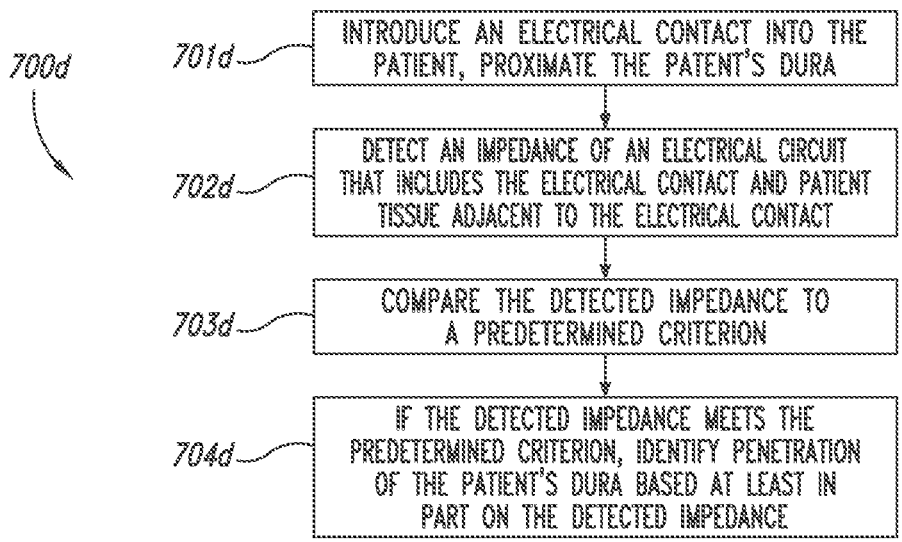

FIG. 7D illustrates a process 700d that may be used independently of or in conjunction with any of the foregoing methods described above with reference to FIGS. 7A-7C. In particular, the process 700d includes introducing an electrical contact into a patient, proximate to the patient's dura (process portion 701d). In process portion 702d, an impedance of an electrical circuit that includes the electrical contact and patient tissue adjacent to the electrical contact is detected. Process portion 703d includes comparing the detected impedance to a predetermined criterion (e.g., a threshold impedance value). If the detected impedance meets the predetermined criterion, then the process 700d can include identifying penetration of the patient's dura based at least in part on the detected impedance (process portion 704d). As discussed above, penetration can include breaking the continuity of the dura, whether or not the electrical contact actually passes through the dura to an intrathecal location. As was also discussed above, the predetermined criterion can include an impedance value at or below which detected impedances correspond to exposure to cerebral spinal fluid. An advantage of the foregoing methodology (and associated computer readable media and methods for programming the computer readable media) is that the practitioner can receive an early indication that the dura has been penetrated, and can take appropriate corrective action. Corrective actions include re-positioning the signal delivery device and possibly repairing damaged dural tissue.

From the foregoing, it will be appreciated that specific embodiments of the technology have been described herein for purposes of illustration, but that various modifications may be made without deviating from the technology. For example, in other embodiments, the foregoing systems and methods can be used to locate devices other than spinal cord implants. In a particular embodiment, the intrathecal detection device and methodology described above can be applied to other areas of the patient's body that are surrounded by the dura and contain cerebral spinal fluid, for example, the brain. In still further embodiments, these devices and methodologies can be applied to implantable patient devices other than neural modulators (e.g., other elements configured for patient implantation, with therapy contacts in at least some cases). The implanting tools described above can have configurations other than a stylet (e.g., a catheter) in other embodiments. The locator signal emitters and/detectors can be omnidirectional in certain embodiments or can be unidirectional in other embodiments. In certain embodiments, phase shift and/or phased array techniques can be implemented to enhance system efficacy. The signal delivery system can include one transmission device in certain embodiments, and more than one transmission device in other embodiments.

Certain aspects of the technology described in the context of particular embodiments may be combined or eliminated in other embodiments. For example, the display 170*a* described above with reference to FIG. 5 may in some embodiments be made thin and flexible enough to be placed directly on the patient's body, with the detector elements integrated into the display medium. Accordingly, the practitioner can obtain the benefit of a graphical representation of the implanted signal delivery device, together with the proximity of the display to the actual location of the signal delivery device. The use of an aural indicator described above in the context of the intrathecal penetration detector can be applied to the technique for locating the signal delivery device relative to other motion axes, in addition to or in lieu of presenting the information via a visual display. For example, the aural indication can be triggered if the signal delivery device exceeds a threshold distance from the patient's midline. Further, while advantages associated with certain embodiments have been described in the context of those embodiments, other embodiments may also exhibit such advantages and not all embodiments need necessarily exhibit such advantages to fall within the scope of the present disclosure. Accordingly, the disclosure and associated technology can encompass other embodiments not expressly described or shown herein.

We claim:

1. A patient treatment system, comprising:
   a signal delivery system that includes a patient-implantable signal delivery device coupleable to a signal generator that generates and delivers a neural modulation therapy signal having therapy signal parameters including a frequency in a frequency range, a pulse width in a pulse width range, and an amplitude in an amplitude range; and
   an array of external signal detector elements and display elements that is movable relative to the signal delivery device, the external signal detector elements being configured to wirelessly detect signals having the therapy signal parameters delivered by the signal delivery device through the patient's skin, the display elements being operatively coupled to the signal detector elements to display data based on information provided by the detector elements.

2. The treatment system of claim 1, further comprising the signal generator, wherein the signal generator is coupleable to a power source to generate the therapy signal.

3. The treatment system of claim 2, further comprising the power source, wherein the power source transmits power to the signal generator using electromagnetic induction.

4. The treatment system of claim 2, further comprising the power source, wherein the power source includes an external coil that communicates with an internal coil within the signal generator.

5. The treatment system of claim 2, further comprising the power source, wherein the power source is portable.

6. The treatment system of claim 1 wherein an individual display element is co-located with a corresponding individual external signal detector element to present an indication of a signal strength detected at the corresponding external signal detector element.

7. The system of claim 1, further comprising a computer-readable medium containing instructions that, when executed, interpolate results obtained from the plurality of signal detector elements to identify an estimated position of the signal delivery device.

8. The treatment system of claim 1, further comprising an insertion tracker operably coupleable to the signal delivery system to track a length of the signal delivery system inserted into the patient.

9. The treatment system of claim 8 wherein the insertion tracker includes an electromechanical device that is releasably engageable with the signal delivery system.

10. The treatment system of claim 1, further comprising a computer-readable medium containing instructions that, when executed, generate and transmit the neural modulation therapy signal.

11. The treatment system of claim 1 wherein the array has at least one releasable fixation element positioned to releasably secure the array to the patient's skin.

12. The treatment system of claim 1 wherein the array is carried by a flexible, conformable support member.

13. The treatment system of claim 1, further comprising the signal generator, wherein the signal generator includes a pulse generator.

14. The treatment system of claim 1 wherein the frequency range is from about 3 kHz to about 50 kHz.

15. The treatment system of claim 1 wherein the signal delivery device includes a lead having an axial opening.

16. The treatment system of claim 15 wherein a therapy contact is positioned toward a distal end of the lead.

17. A method for treating a patient, comprising:
   emitting a signal from a therapy signal delivery system positioned beneath a patient's skin, the signal delivery system including a signal delivery device having at least one electrical contact, wherein:
      the signal delivery device is coupled to a signal generator that generates the signal, and
      the signal has therapy signal parameters including a frequency in a frequency range, a pulse width in a pulse width range, and an amplitude in a amplitude range;
   wirelessly detecting the signal from external to the patient via an array of moveable signal detector elements; and
   presenting display data at an array of display elements, based on information provided by the array of signal detector elements.

18. The method of claim 17 wherein emitting the signal includes directing the signal to treat pain in the patient.

19. The method of claim 17 wherein emitting the signal includes emitting the signal from the signal delivery device.

20. The method of claim 17 wherein individual signal detector elements receive corresponding individual indications of the strength of the signal.

21. The method of claim 17 wherein the array of signal detector elements is releasably carried by the patient.

22. The method of claim 17, further comprising releasably attaching the array of signal detector elements to the patient's skin.

23. The method of claim 17, further comprising detecting a location of the signal delivery device based at least in part on detecting the signal.

24. The method of claim 23 wherein detecting the location includes detecting a lateral location and a rostral/caudal location.

25. The method of claim 23 wherein detecting the location includes detecting a dorsal/ventral location.

26. The method of claim 17 wherein the frequency range is from about 3 kHz to about 50 kHz.

27. The method of claim 17 wherein presenting display data is performed during a process for implanting the signal delivery device.

\* \* \* \* \*

UNITED STATES PATENT AND TRADEMARK OFFICE
CERTIFICATE OF CORRECTION

PATENT NO. : 11,382,531 B2
APPLICATION NO. : 16/287486
DATED : July 12, 2022
INVENTOR(S) : James R. Thacker et al.

It is certified that error appears in the above-identified patent and that said Letters Patent is hereby corrected as shown below:

On the Title Page

On the page 5, in Column 2, item (56) under "Other Publications", Line 4, delete "Cliniciam" and insert -- Clinician --.

In the Specification

In Column 1, Line 17, delete "HELD" and insert -- FIELD --.

In Column 13, Line 13, delete "practitioners" and insert -- practitioner's --.

Signed and Sealed this
Eighteenth Day of July, 2023

Katherine Kelly Vidal
*Director of the United States Patent and Trademark Office*